United States Patent [19]
Anderson et al.

[11] Patent Number: 5,595,568
[45] Date of Patent: Jan. 21, 1997

[54] PERMANENT HAIR REMOVAL USING OPTICAL PULSES

[75] Inventors: R. Rox Anderson, Lexington; Melanie Grossman, Boston; William Farinelli, Danvers, all of Mass.

[73] Assignee: The General Hospital Corporation, Boston, Mass.

[21] Appl. No.: 382,122

[22] Filed: Feb. 1, 1995

[51] Int. Cl.⁶ .................................................. A61N 5/06
[52] U.S. Cl. .................................................. 606/9
[58] Field of Search ................. 606/9, 10, 11, 606/12, 17, 14, 15, 16

[56] References Cited

U.S. PATENT DOCUMENTS

| | | | |
|---|---|---|---|
| 3,538,919 | 11/1970 | Mever et al. | 128/398 |
| 3,693,623 | 9/1972 | Harte et al. | |
| 3,834,391 | 9/1974 | Block. | |
| 3,900,034 | 8/1975 | Katz et al. | 128/395 |
| 4,461,294 | 7/1984 | Baron. | |
| 4,608,978 | 9/1986 | Rohr. | |
| 4,617,926 | 10/1986 | Sutton. | |
| 5,000,752 | 3/1991 | Hoskin et al. | 606/9 |
| 5,057,104 | 10/1991 | Chess | 609/9 |
| 5,282,797 | 2/1994 | Chess | 609/9 |
| 5,425,728 | 6/1995 | Tankovich | 606/9 |
| 5,474,549 | 12/1995 | Ortiz et al. | 606/9 |
| 5,486,172 | 1/1996 | Chess | 606/9 |

FOREIGN PATENT DOCUMENTS

WO86/02783 9/1986 WIPO.

Primary Examiner—Angela D. Sykes
Assistant Examiner—Sonya Harris-Ogugua
Attorney, Agent, or Firm—Wolf, Greenfield & Sacks, P.C.

[57] ABSTRACT

A method and apparatus for simultaneously removing multiple hair follicles from a skin region of a patient. The method includes the step of illuminating the hair follicles with a large-area, optical radiation field by way of a transparent contact device proximal to the skin region. This allows portions of the hair follicles to be heated and then removed, while the surrounding skin region is left relatively free of injury.

22 Claims, 7 Drawing Sheets

(Dry Hair)

(Wet Hair)

(Skin)

PERMANENT HAIR REMOVAL USING OPTICAL PULSES

This invention was made with Government support under Contract N00014-91-C-0084 awarded by the Department of the Navy. The Government has certain rights in the invention.

BACKGROUND

This invention relates to hair-removal methods using optical radiation.

Unwanted hair is a common dermatological and cosmetic problem, and can be caused by heredity, malignancy, or endocrinologic diseases such as hypertrichosis (i.e., excess hair) and hirsutism (i.e., androgen-influenced hair). Hair can be temporally removed using a number of techniques including wax epilation, depilatory creams, and, of course, shaving. Alternatively, hair can be permanently removed using electrolysis; this process involves insertion of a current-carrying needle into each hair follicle, and is often painful, inefficient, and time consuming.

Optical-based methods, such as the use of laser light, have also been used for hair removal. U.S. Pat. No. 4,388,924, for example, describes irradiation of individual hair follicles using a laser; in this method, heating of the hair's root section causes coagulation in local blood vessels, resulting in removal of the follicle. Related techniques, such as those described in U.S. Pat. No. 5,226,907, involve removal of the follicle by first applying a light-absorbing substance to the region of interest, and then irradiating the substance to heat and remove the follicle.

SUMMARY OF THE INVENTION

In general, in one aspect, the invention provides a method of simultaneously removing multiple hair follicles from a skin region of a patient. The method includes the step of illuminating the hair follicles with a large-area optical radiation field delivered from a transparent contact device positioned proximal to the skin region. This allows heating of portions of the hair follicles so that they are removed, while the surrounding skin region is left substantially free of injury.

In preferred embodiments, during the illuminating step, the contact device is in direct contact with the skin region. A substantially transparent substance (e.g., lotion, oil, water, or an emollient) having desirable optical (e.g., refractive index or transmissivity) and thermal (e.g., thermal conductivity, heat capacity) properties may also be applied to the skin prior to illuminating the region with the contact device. In other embodiments, the contact device is cooled to a low temperature (e.g., between about 4°–15° C.) in order to increase the damage threshold of the skin region, thereby further preventing injury during the illumination step. In addition, during the illumination step, the contact device preferably focusses the optical radiation onto the skin region to heat portions of the hair follicle; most preferably, the optical radiation is focussed below the follicles' papillae.

The spatial and temporal properties of the optical field are optimized in order to maximize the heat deposition in the hair follicle, while reducing damage to the surrounding skin. In preferred embodiments, the optical radiation is pulsed. Preferably, in this case, the pulse duration is between 50 µs and 200 ms, and is most preferably between 10 and 30 ms. The wavelength of the optical radiation is chosen to be selectively absorbed by hair follicles, and is preferably between 680 and 1200 nm; in especially preferred embodiments, the wavelength is between 800 and 900 nm, or, alternatively, between 1000 and 1200 nm. The area of the radiation field is large enough to allow irradiation of multiple hair follicles with a single laser shot, and is preferably at least 0.5 cm$^2$. In especially preferred embodiments, the field's area is between 0.75 and 1 cm$^2$. Each pulse preferably has an energy of between 10 and 200 J/cm$^2$, and most preferably between 30 and 50 J/cm$^2$.

In another aspect of the invention, the contact device is not used, and the radiation field has the preferred pulse width, wavelength, spatial profile, and energy level described above.

The method of the invention is carried out using a device which includes means (e.g., a laser) for generating optical radiation, and an irradiating unit including a contact device for receiving and then delivering the radiation to the skin region of the patient. The contact device consists essentially of a large-area, optically transparent material, and includes a surface shaped to simultaneously contact multiple hair follicles in the skin region.

The surface of the contact device can be either convex or substantially flat; preferably, the device is configured so that the light field entering the skin region is convergent. The contact device may be a lens composed of an optically transparent material selected from the group including sapphire (most preferred), quartz, fused silica, polymeric materials, and glass. In all cases, the optically transparent material preferably has a refractive index roughly matched to that of the skin region.

The invention allows for permanent hair removal in a painless and rapid fashion while sparing the surrounding skin layers (e.g., the dermis and epidermis) from injury. Moreover, optical fields having the preferred parameters described above allow selective destruction of multiple hair follicles using a single or time-dependent sequence of laser shots. This technique, as opposed to irradiating individual hairs in a sequential fashion, significantly expedites the hair-removal process.

Use of a contact device having the desired optical properties is preferred because it allows efficient coupling of the light field onto the skin region to be irradiated. Once the light field is delivered, a contact device having desired thermal properties additionally facilitates heat transfer out of the irradiated skin region, thereby reducing injury to the epidermal layer.

Because the hair-removal method of the invention selectively deposits heat onto the hair follicle via optical absorption, the method is most efficient when used with patients having dark, highly pigmented (i.e. strongly absorbing) hair and relatively white (weakly absorbing) skin. Fortunately, a majority of patients desiring hair removal have this coloring.

Other features and advantages of the invention will be apparent from the following description of the preferred embodiments thereof, and from the claims.

DETAILED DESCRIPTION

Figure 1:
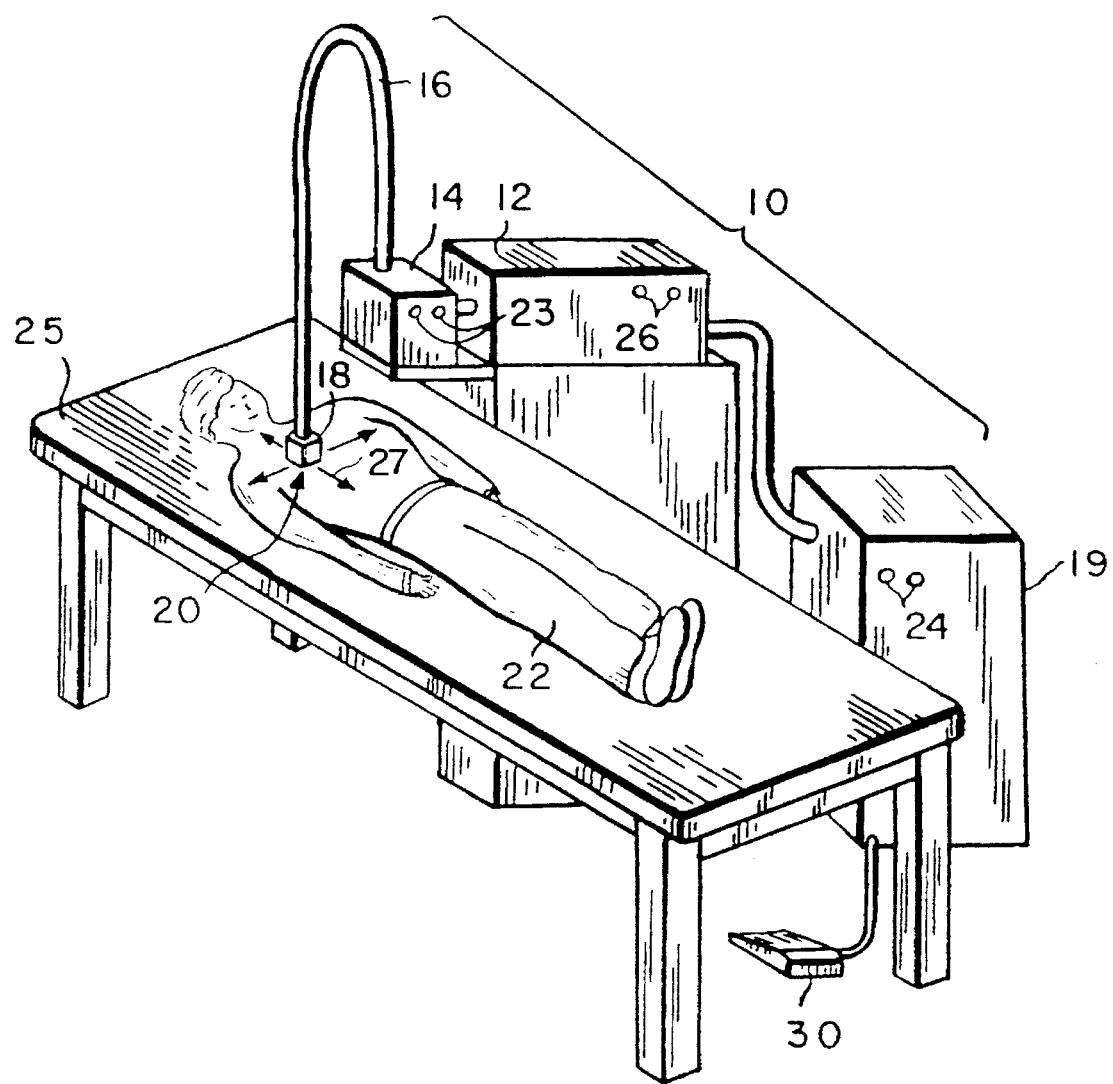
FIG. 1 is a perspective view of the laser-based hair-removal device according to the invention.

Referring to FIG. 1, a laser-based hair-removal system 10 includes a light source 12, which may, for example, include one or more lasers for generating the irradiating field. The light source 12 is preferably optically coupled to a series of beam-manipulating optics 14 which, in turn, may be coupled via a fiber optic cable 16 (or other fiber optic device) to the irradiating unit 18. During the hair-removal therapy, the light source is powered by a voltage and current supply 20, and delivers a beam of light through the optics 14 and fiber optics 16 to the irradiating unit 18. The field is then delivered to a region 20 of a patient 22 (positioned, for example, on a platform 25) resulting in hair removal from the region 20. Once the desired region is treated, the region is inspected by the operator to determine the degree of hair removal; the irradiating unit can then be easily moved along the patient 22, as indicated by arrows 27, and used to treat subsequent regions.

The spatial and temporal properties of the optical field determine the efficacy of the hair-removal process, and may be adjusted using a series of controls 24, 26, 28 located on various components of the hair-removal system 10. For example, using controls 24 located on the power supply, the optical intensity and pulse repetition rate of the irradiating field can be controlled by adjusting parameters such as the supplied voltage, current, and power supply switching rate. Other properties of the field, such as the wavelength and pulse duration, may be varied by controls 26 which adjust components (e.g., gratings, mirror or filter positions, shutters, or pulse-forming means) of the light source 12. Similarly, controls 28 can be used to adjust the modulating optics 14, resulting in control of properties such as mode quality, beam diameter, and coupling of the irradiating field into the fiber optics 16. All controls may be adjusted by hand, or, alternatively, by using a foot pedal 30 connected to the system 10.

In alternate embodiments, the light source, coupling optics, and irradiation unit may be encompassed in a single, hand-held device. In this case, the light source is preferably an array of diode lasers coupled directly to the irradiating unit, and is powered by a small external power supply. The compact nature of this type of optical system allows for a more controllable, maneuverable device, and additionally obviates the need for fiber optic delivery systems.

In order to effectively destroy the irradiated hair follicles without causing damage to the surrounding skin, the light field supplied by the system 10 and the irradiating unit 18 is designed to maximize the amount of light-induced heat deposited in the hair follicles, while reducing the degree of injury to the surrounding skin. It is preferred, for example, to deliver sufficient optical energy to several "target" regions on the hair follicle; radiation delivered to these regions results in complete and localized destruction of the hair.

Prior to treatment, the region to be treated may be shaved in order to facilitate hair removal. Following treatment, patients may be treated with topical antibiotic ointments.

Mechanical Structure

Figure 2A:
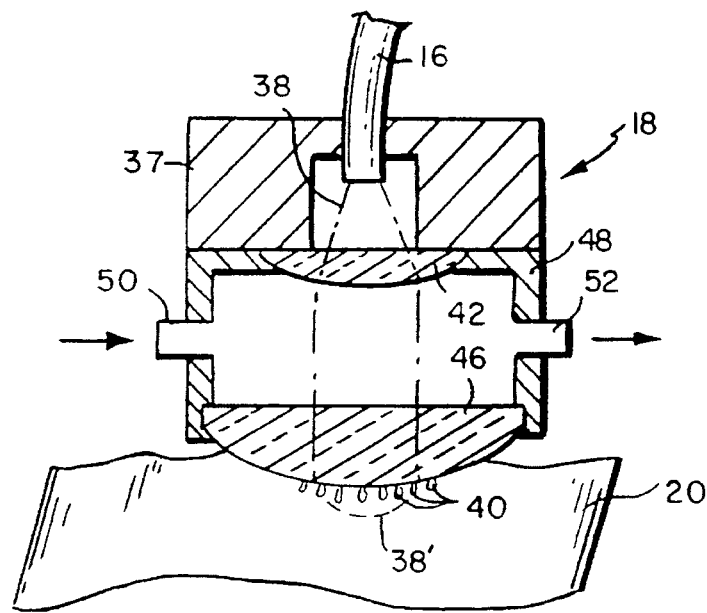
FIGS. 2A and 2B are cross-sectional views of the irradiating unit of the hair-removal device receiving, respectively, light from a fiber optic or fiber optic bundle, and from a mirror assembly.
Figure 2B:
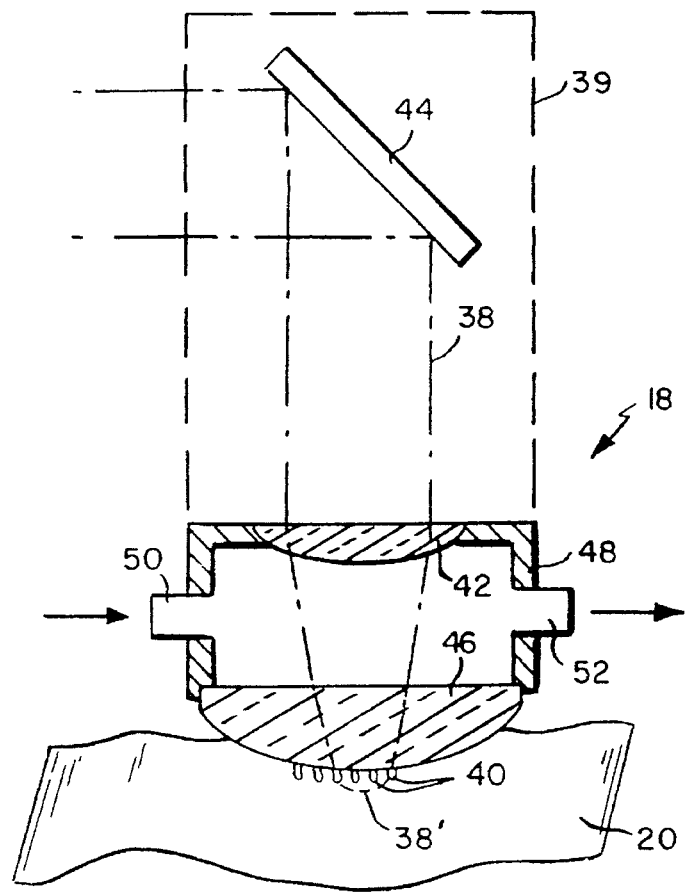

With reference now to FIGS. 2A and 2B, the irradiating unit 18 of the hair-removal system allows delivery of the irradiating field 38 to hair follicles 40 located in the region 20. As shown in FIG. 2A, the field 38 may be delivered to the irradiating unit 18 using a fiber optic cable 16 (or other fiber optic device) containing one or more fibers or fiber optic bundles. In this case, after exiting the waveguide, the field 38 is typically spatially dispersed, and is preferably collected and roughly collimated using a plano-convex lens 42. Alternatively, as shown in FIG. 2B, the field may be delivered to the irradiating unit using, for example, one or more reflecting mirrors 44. This allows the field 38 to be roughly collimated prior to impinging the lens 42. Depending on the focal length of the lens 42 and the mode quality of the irradiating field, the field is preferably condensed using, e.g., a plano-convex lens as shown in the figure. After passing through this optic, the beam then impinges a contact device 46 which is preferably placed in contact with the skin region 20. The optical, mechanical, and thermal properties of the contact device 46 are chosen to allow efficient coupling of the optical radiation into the skin region (resulting in a delivered field 38'); once delivered, the field is used to irradiate, heat, and then remove the hair follicles 40. The contact device 46, in addition, is used to couple light and heat out of the superficial skin layer (i.e., epidermis) of the irradiated region. This allows the light-absorbing pigment (i.e., melanin) contained within the deep part of the hair follicles to be irradiated and selectively heated, permitting permanent destruction of the follicle, while potentially deleterious optical and thermal energy are simultaneously conducted out of the overlying skin layers. Thus, multiple hair follicles can be permanently removed from the skin region without causing pain or injury to the patient.

Both the lens 42 and contact device 46 are preferably disposed in a housing 48 containing both entrance 50 and exit 52 ports for fluids such as cooling water or purge gas to flow into and out of; fluids may be used, for example, to cool the contact device 46, which, in turn, allows the skin surface to be cooled. Alternatively, the housing 48 may include an electrically controlled cooler in order to provide accurate control over the temperature of the contact device 46. Preferably, when cooling means are used, the temperature of the skin is reduced to between 4°–15° C. In addition, in this case, it is preferred that a short time period (e.g., about 1 second) be allowed to elapse before irradiation in order to ensure that the skin is adequately cooled. An external casing 39, as indicated in FIG. 2B by the dashed line, or a fiber-coupling housing 37, as shown in FIG. 2A, may be used to connect the light-delivering means to the housing 48.

Figure 3A:
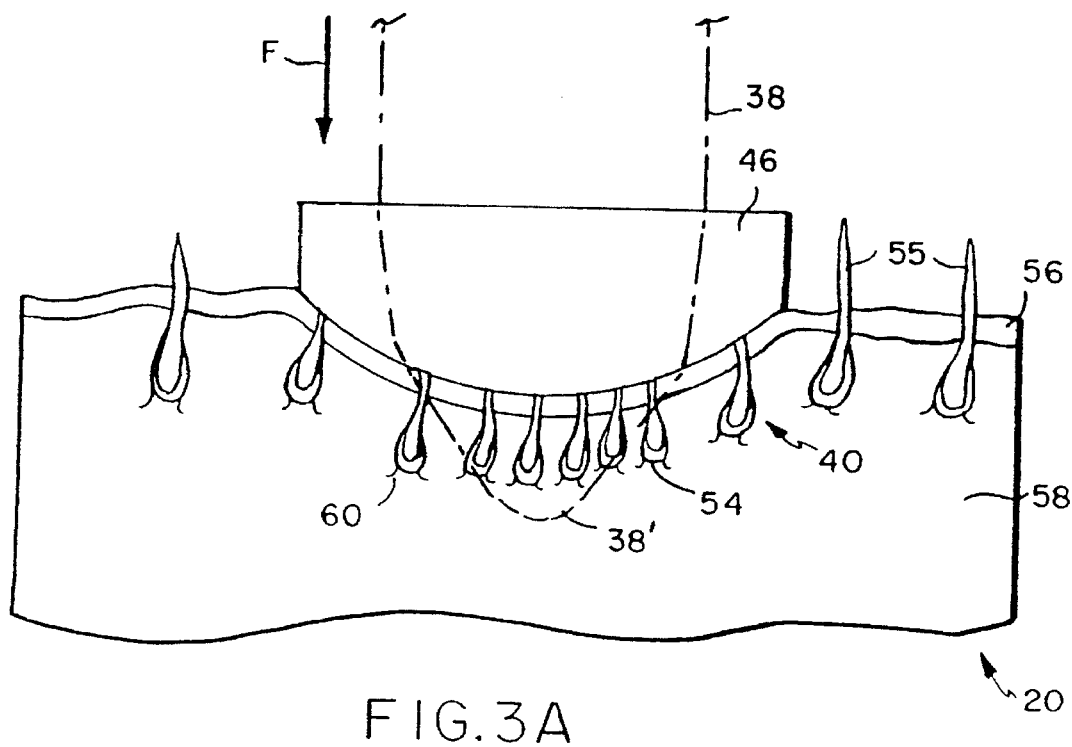
FIGS. 3A, 3B, and 3C are, respectively, an expanded, cross-sectional view of the contact device of the irradiating unit in direct contact with a hair-containing skin region, a cross-sectional, cut-out view showing the back-scattered optical fields at the contact device/epidermis interfacial region, and a cross-sectional, cut-out view showing thermal transport at the interfacial region.

With reference now to FIG. 3A, the contact device 46 is preferably formed into a lens shape in order to converge the irradiating field near the base of the hair follicles 40. In order to focus light, the contact device must be optically transparent at the irradiating wavelength, and preferably has a biconvex or plano-convex lens shape, preferably with an f number less than or equal to F/1.0, and a focal length of between about 0.5 and 2 cm. Control over the surface shape of the contact device allows the focussed light field 38' to simultaneously irradiate various target portions of the hair follicle, resulting in efficient destruction. Typically, each irradiated hair shaft has a diameter of about 75 microns, with the entire follicle having a diameter of about 200 microns. After passing through the contact device 46, the light field 38' is preferably focussed through the epidermis 56 of the skin layer (having an thickness, e.g., of about 0.1 mm) and is condensed in the dermis 58 near the papillae 54 of the follicles 40. Because dermal thickness varies greatly over the body, the papillae may be superficial (as in, e.g., the eyelids and scrotum), but for most areas of interest (e.g., the face, axillae, and legs) the papillae are located at depths of approximately 4 to 7 mm beneath the epidermal surface. Located a few tenths of a millimeter below the papillae are neurovascular bundles 60 which serve the metabolic and other needs of a hair matrix, the region of rapidly growing keratinizing cells, located in the papilla, which produce the hair shaft 55. The matrix, papilla, and the corresponding vascular bundle represent the follicular targets to be irradiated. Preferably, during irradiation of these regions, the field is focussed so that damage is localized to a small region of dermis (typically within about 0.2 mm) surrounding each follicle. The extent of damage is preferably much less than half the distance between neighboring follicles (typically between 1 and 4 mm); if it is significantly greater than this, the light-induced injury may result in a third-degree burn.

In addition to providing a focussing function, a contact device 46 having a convex-shaped surface 62 allows efficient compression of the skin during contact. Compression of the dermis 58 located near the surface 62 of the contact device decreases the distance between this region and the papillae; depending on the force applied, the distance may be decreased by several millimeters. Because the radiation field 38' is scattered and correspondingly attenuated during propagation through the dermis, compression of the skin results in more efficient light-induced heating of the papilla. In addition, compression of the dermis by the contact device using a pressure greater than the patient's blood pressure forces light-absorbing blood out of the irradiated region (indicated during treatment by a whitening of the skin in the pressurized region). This reduces absorption of the optical field, resulting in more efficient delivery of light to the follicular target regions. Pressure applied using a contact device having a convex surface results in a relatively uniform displacement of blood from the skin region. A contact device having this shape is therefore preferred to a flat device, which tends to produce regions having center portions which are not entirely blood-free.

In alternate embodiments, the contact device may be mounted in the housing in a spring-loaded fashion so that it may be forced against the skin surface with an adjustable pressure. In addition, in this embodiment, the spring mechanism may be attached to a sensor and readout device so that the exact pressure applied to the skin surface can be accurately monitored.

Figure 3B:
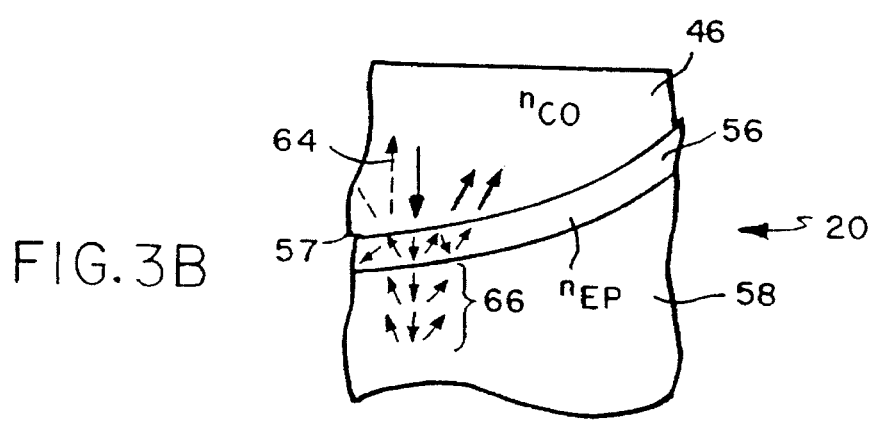

When forced against the skin, the contact device 46 allows optical radiation to be coupled into and out of the epidermis. With reference now to FIG. 3B, the refractive index ($n_{CD}$) of the contact device 46 should be approximately matched to that ($n_{EP}$) of the epidermis 56, which is approximately 1.55. Because light travelling from one refractory medium (i.e., the contact device) to another (the epidermis) is reflected at the interface 57 separating the two regions by an amount related to the square of the refractive index difference, nearly index-matching allows efficient coupling of the irradiating field into the skin. Thus, a contact device composed of a material having a refractive index near 1.5 allows the incident irradiating field to undergo minimal reflections (indicated in the figure by the arrow 64) at the epidermis/contact device interface 57. Similarly, as indicated in the figure by the arrows 66, optical fields within the dermis are back-scattered towards the epidermis due to diffuse reflectance. These back-scattered fields contribute to unwanted epidermal heating, and are easily coupled out of the skin using the index-matched contact device 46. This allows minimization of the light-induced damage to the epidermis 56, while allowing effective irradiation of the follicle target sites within the dermis. In preferred embodiments, in order to be index-matched, the contact device is preferably formed of a high-density material such as sapphire ($n_{CD}$=1.7), fused quartz ($n_{CD}$=1.5), fused silica, or similar optically transparent glasses or plastics.

Figure 3C:
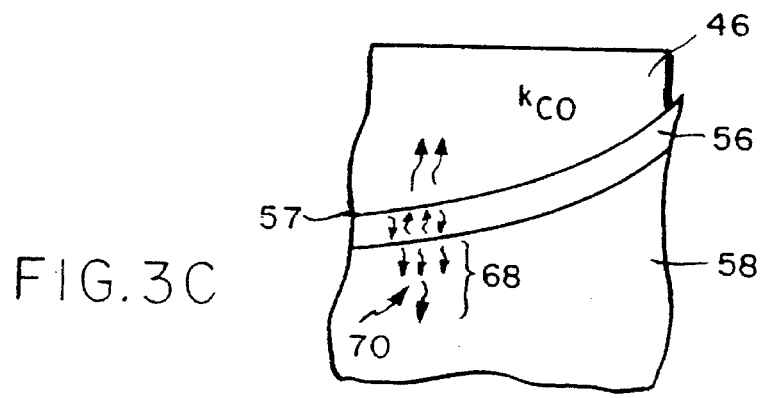

With reference now to FIG. 3C, in order to conduct heat away from the epidermis, it is additionally preferred that the contact device 46 be composed of a material having a high thermal conductivity ($\kappa_{CD}$) which is similar to that of the skin. This allows efficient transfer of heat (indicated in the figure by the arrows 68) from the epidermis 56, across the contact device/epidermis interface 57, and into the contact device 46. A high thermal conductivity, in addition, is necessary to minimize local heating effects that may occur at the interface 57, thereby reducing the chance of thermally induced damage or injury to the irradiated epidermis. Ideally, the thermal properties of the contact device allow minimization of the heating near the epidermis, but have little effect on heat deposited near the papillae of the hair follicle (shown in the figure as the region 70). Materials having high thermal conductivities include sapphire ($K_{CD}$= 0.083 cal sec$^{-1}$ cm$^{-2}$ °C. cm$^{-1}$ along the C axis at 30° C.), fused quartz ($K_{CD}$=0.026 cal sec$^{-1}$ cm$^{-2}$ °C. cm$^{-1}$ along the C axis at 30° C.), as well as other high-density glasses and plastics.

In addition, in order to improve both optical (i.e., transmission of back-scattered light) and thermal (i.e., heat conduction) properties at the contact device/epidermis interface 57, it is desirable to apply to the skin a topical liquid or emollient, such as a lotion, water, alcohol, or oil, having a refractive index which is similar to that of the contact device 46 and epidermis. For example, application of an oil having a refractive index between that of the epidermis (n=1.55) and sapphire (n=1.7) minimizes optical reflection effects at the interface, thereby allowing more efficient transfer of back-scattered radiation between these regions. Also, a liquid allows for more efficient transfer of heat into the sapphire, thereby reducing the degree of damage or injury to the epidermis.

Optical Properties

The temporal, spatial, and intensity-dependent properties of the irradiating optical field ultimately determine the amount of heat deposited into the target regions of the hair follicle; these properties, therefore, can be adjusted to optimize the hair-removal process. In particular, properties which affect the hair-removal process include the pulse energy, pulse duration, repetition rate (i.e., the time duration between subsequent pulses), wavelength, energy, exposure spot size, beam convergence as it enters the skin, and mode geometry (i.e., spatial extent and uniformity) of the optical pulse. These characteristics may be controlled according to the pigment present in the hair and skin to be irradiated; preferably, each parameter is adjusted so that the temperature at each target site, immediately following irradiation, is elevated to between about 80° and 120° C. Heating the follicle to this temperature leads to permanent damage and subsequent removal.

Figure 4:
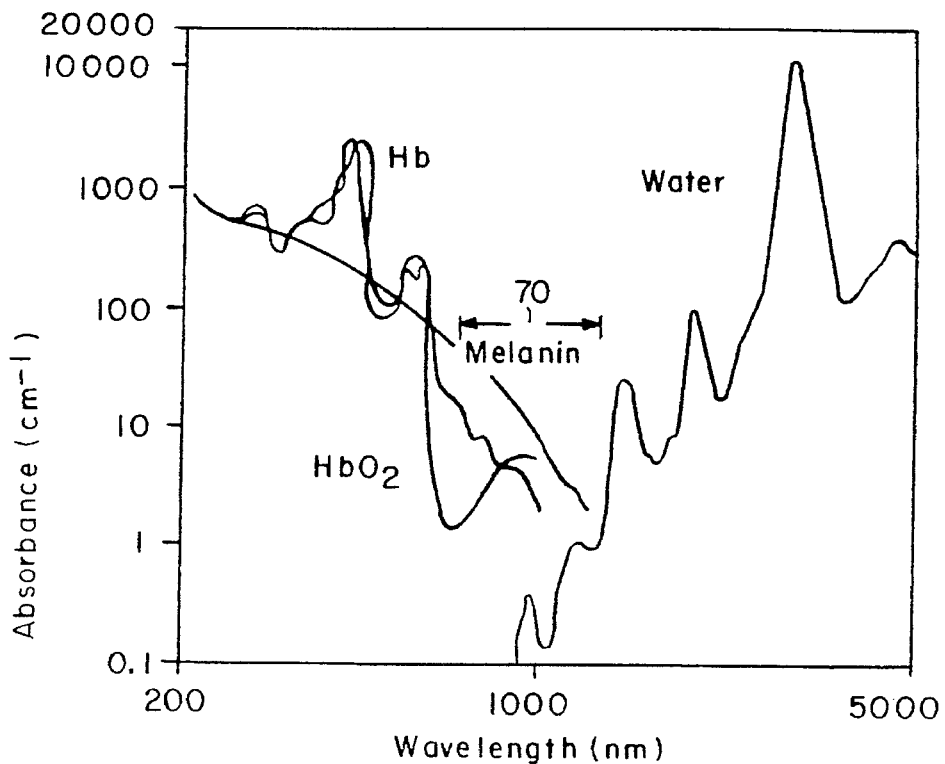
FIG. 4 is a plot showing the optical absorption spectra of melanin, hemoglobin, oxidized hemoglobin, and water.

Referring now to FIG. 4, the wavelength of the irradiating field is chosen to be resonant with the natural pigment (i.e. melanin) present in the target sites (i.e., the hair shaft, matrix, and papilla). The absorption spectra of melanin, water, hemoglobin, and oxy-hemoglobin shown in the figure indicate the ability of these compounds to absorb optical radiation having different wavelengths; low absorption indicates that light at the particular wavelength will penetrate deeper in the absorbing media. In general, in order to selectively heat the target regions, the wavelength of the irradiating field is chosen to match the absorption spectrum of melanin, which absorbs light from about 200 to 1000 nm; conversely, the wavelength is mismatched to the absorption spectra of compounds contained in the skin, such as water and hemoglobin. Light having wavelengths between 680 and 1200 nm, a range indicated by the arrow 70 in the figure, is effectively absorbed by melanin while being relatively transmitted by both hemoglobin and water, and therefore can be used for selective heating of heavily pigmented hair surrounded by white skin. In particular, light in the range of 800 to 900 nm or 1000 to 1200 nm is preferred, as this radiation is strongly absorbed by melanin, and will not be absorbed by the bands present in water and hemoglobin near 950 nm. For patients with thin skin and heavily pigmented hair, wavelengths shorter than 800 nm may be used. In addition, other light-attenuating effects besides absorption, e.g., scattering of radiation, are also wavelength-dependent, and should be considered during selection of the optical field's wavelength. For example, in human skin, the penetration of light is partially determined by the transport scattering coefficient ($\mu_s'$), which decreases at longer wavelengths due primarily to scattering in the dermis. For radiation at 1000 nm, $\mu_s'$ is about 10 cm$^{-1}$; light propagating through the skin at this wavelength will therefore reach a maximum intensity at about 1 mm below the skin surface.

Light sources generating light in the preferred range of 680–1200 nm include diode ($\lambda \approx 800$–1000 nm), Nd:YAG and Nd:YLF ($\lambda = 1064$ and 1053 nm), Ti:Sapphire and infrared dye ($\lambda \approx 700$–1000 nm), ruby ($\lambda = 694$ nm), and alexandrite ($\lambda = 700$–850 nm) lasers. Nd:YAG and diode lasers (particularly arrays of diode lasers) are preferred as these sources are commercially available, well-categorized, and can be manufactured on a small scale. Light sources of this type can be incorporated into compact hair-removal devices which, in turn, can be easily manipulated by the operator during hair-removal procedures.

Figure 5A:
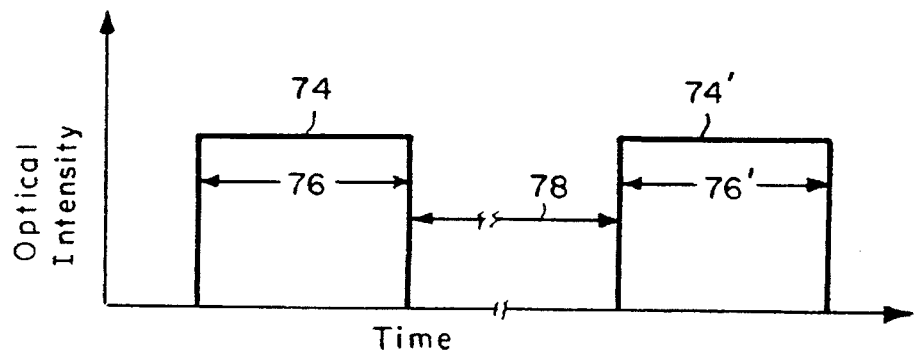
FIGS. 5A and 5B show, respectively, the time and spatial profiles of the preferred optical field used during the hair-removal process.

The duration of the optical pulse can also be controlled in order to vary the heating of the hair follicle. Referring now to FIG. 5A, the optical pulses, indicated by the waveforms 74, 74', preferably have durations 76, 76' which allow the follicle to be heated for short periods of time. The pulse width is controlled to vary the heat conduction during the optical pulse, and thus the damage of the follicle and its immediate surrounding dermis: too little damage results in hair re-occurrence, while extensive damage may produce scarring in the irradiated region. Preferably, the pulse duration 76, 76' is between about 50 µs and 200 ms.

The exact pulse duration is dictated by the diffusion of heat in the skin, a process which roughly follows the heat diffusion equation relating the diffusion time t, diffusion distance d, and thermal diffusivity κ, as discussed by in Welch, A. J. "The thermal response of laser-irradiated tissue", IEEE J. Quant. Electron. QE-21 (12), 1471–1481 (1984): $t = d^2/4\kappa$ (κ for the human dermis is roughly $1.3 \times 10^{-3}$ cm$^2$/sec). At times longer than a few hundred milliseconds, too much thermal diffusion may occur during the exposure period, resulting in either incomplete destruction of the target regions of the hair follicle, excessive dermal damage, or both.

The intensity of the optical field is inversely related to the pulse duration; thus, when the pulse duration is below about 10 µs, large optical intensities may result in undesirable damage to surrounding skin regions. In addition, short pulses may result in localized heat-induced "explosions" in the follicle which cause mechanical damage to the skin. In particularly preferred embodiments, the pulse has a width of about 10–30 ms. During this time period, thermal diffusion takes place over a distance of about 0.1 mm; damage confined to about this distance results primarily in destruction of the irradiated hair follicles, and not to the surrounding skin.

Optical pulses having well-defined and adjustable durations may be generated using known techniques. For instance, intra-cavity modulation of the light field using electro or acousto-optic Q-switching devices allows generation of pulses having temporal profiles which are typically Gaussian in shape. Pulses made using these methods are typically too short, however, having durations in the sub-microsecond range. Normal-mode pulses produced by flashlamp excitation of ruby, alexandrite, Ti:sapphire, or Nd:YAG lasers are preferred because these typically are high-energy pulses in the 0.1–10 ms pulse duration region. Alternatively, a continuous (i.e., time-independent) optical field emitted by a laser can be externally modulated using, for example, a mechanical shutter or electro-optic gate. Modulation using external methods is desirable, as this allows the pulse width to be easily varied from a few hundred microseconds to several hundred milliseconds. Pulses generated using external modulation typically have "square wave" temporal profiles (as shown in FIG. 5A) which allow a more uniform optical field to be applied to the region of interest.

When a contact device is used to deliver the optical pulse, a time delay preferably exists between the arrival of the pulse and the time at which the contact device contacts the skin surface. This allows the outer, epidermal surface to be cooled significantly prior to irradiation, thereby increasing its damage threshold relative to that of the lower-lying papillae.

In addition, the time duration between optical pulses (indicated in FIG. 5A by the arrow 78) may be adjusted in order to control the amount of heat deposited into the irradiated region. If repetitive illumination is required for destruction of the follicle, this time period is preferably constant and lies between several seconds and a few hundred milliseconds. Alternatively, for "single shot" illumination, this time period is selectively controlled by the operator. In this case, a single laser shot is delivered to the region of interest, and then the region is inspected by the operator for damage. If more radiation is required to remove unwanted hairs, additional laser shots can then be delivered to the region. Otherwise, the irradiation unit is translated and used to treat a separate region.

Figure 5B:
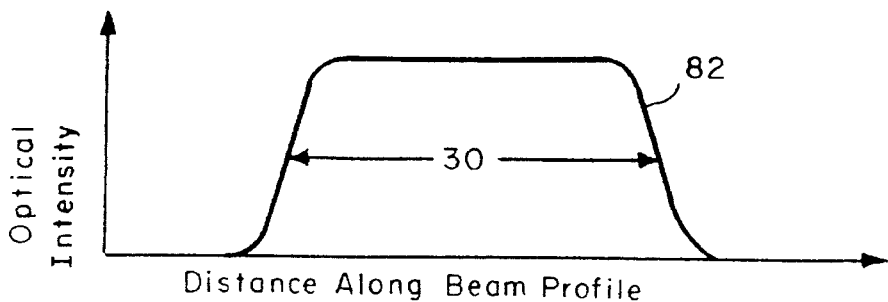

The spatial extent of the optical field is chosen to allow multiple hair follicles to be irradiated with a single laser shot. In addition, larger spot sizes are preferred as attenuation due to scattering decreases as the beam radius, R, increases. Thus, wide-area beams allow more efficient delivery of optical radiation to the target sites. Referring now to FIG. 5B, the width 80 of the spatial profile 82 of the irradiating beam at the surface of the skin is preferably on the order of, or greater than, the depth of the target to be irradiated. Most preferably, the beam diameter is at least 8 mm. The area of the irradiating field is preferably between about 0.5 and 1.2 cm$^2$, and is most preferably between 0.75 and 1 cm$^2$. Because the beam is preferably focussed into the skin, the spatial profile will be gradually condensed as a function of depth before reaching a waist in the vicinity of the papillae. Preferably, as shown in FIG. 5B, the intensity across the beam diameter is roughly constant in order to provide a substantially uniform irradiating field.

Figure 6:
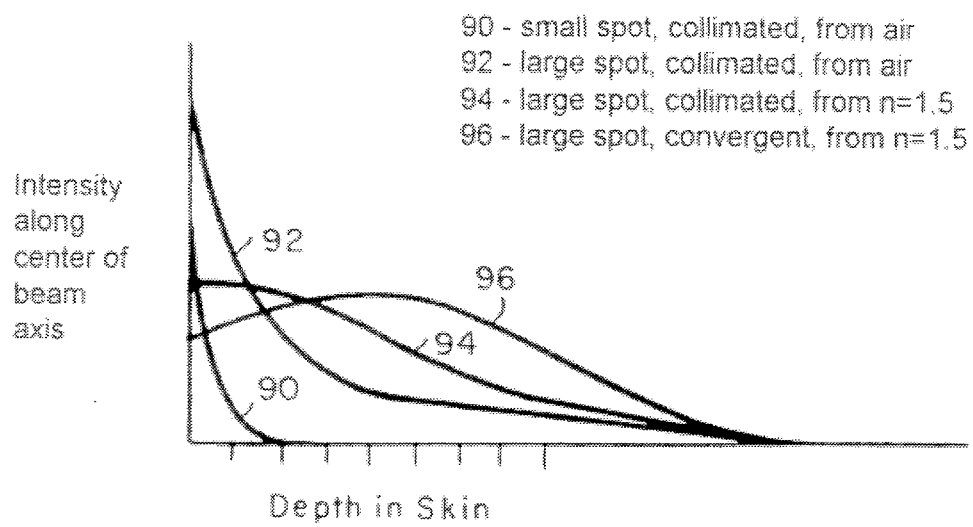
FIG. 6 is a plot of the computer-generated optical intensity as a function of skin depth for different optical fields.

Referring now to FIG. 6, following illumination, the intensity distribution of optical radiation (i.e., the dimensionless y axis in the figure) as a function of skin depth (i.e., the dimensionless x axis) is calculated using Monte Carlo-based computer simulations. The distribution is a function of the beam's spatial profile and the refractory properties of the medium in contact with the skin. Although the plotted data is based on a computer simulation, and is thus only an approximate, the x axis units are estimated to be about 500 microns per tick mark. The first curve 90 shows the skin depth-dependent properties of an optical field originating from a small, collimated spot in air. In this case, the majority of the optical intensity is distributed near the surface of the skin (indicated by the "0" point along the x axis), with the intensity dropping off rapidly at larger depths. A larger, collimated spot originating from air (curve 92) has a more evenly distributed skin depth-dependent intensity, although the majority of the light is still concentrated near the skin surface. Delivering a large, collimated radiation spot from a material having a refractive index of 1.5 (curve 94) results in a relatively uniform optical intensity in the first millimeter or so of the skin; at larger depths, this intensity starts to tail off with a relatively slow time constant. Finally, in the preferred embodiment, a large, spatially converging optical field from the n=1.5 refractory material has a relatively low intensity at the skin surface which increases to a maximum after propagating a few millimeters into the skin. The intensity then attenuates as a function of skin depth with a time constant slower than that exhibited by the curve 94. Thus, a field of this type can be used to effectively heat the target sites of the follicle, while sparing the skin at the surface from injury.

In the case where the illuminating laser generates a beam having a diameter less than the preferred values, it may be necessary to expand the beam prior to delivery to the irradiating unit. This may be done with conventional telescoping optics, e.g. two-lens systems configured to first expand and then collimate the emitted beam. Alternatively, as shown in FIG. 2A, the irradiating field may be coupled into an optical fiber and then delivered to the irradiating unit. In this case, the emerging field is naturally dispersed due to the waveguide nature of the fiber, and is then collected by a collimating lens. Displacement of the lens from the fiber tip allows the irradiating beam's profile to be increased to the desired amount.

The fluence of the optical field will be varied according to the degree of pigmentation in the patient, and is preferably between about 10 and 200 J/cm$^2$ for each pulse; patients with darker hair will require light of lower fluence than patients with lighter hair. Most preferably, the pulse energy of the irradiating field is between 30 and 50 J/cm$^2$. As described herein, in all cases, the fluence is adjusted in order to heat the target regions to the desired temperature of approximately 80° to 120° C. Moreover, the level of fluence is preferably increased as the pulse duration is increased in order to compensate for less efficient heating of follicles due to heat conduction during long pulses. It may be necessary to increase or decrease the optical fluence in order to heat the hair follicle to the desired temperature if the wavelength of the irradiating light field does not lie in the preferred spectral regions (i.e., 800–900 nm or 1000–1200 nm). In addition, in cases where the laser output is below the desired optical fluence, it may be necessary to amplify the individual pulses prior to irradiating the skin. Optical amplifiers, such as external optical cavities, may be used for this purpose.

Table 1, shown below, lists the preferred parameters of the optical fields used for hair removal. The value of each parameter depends on the amount of hair in the region of interest, the degree of pigmentation of the hairs, and the pigmentation of the surrounding skin of the patient.

TABLE 1

| Preferred Optical Field Parameters | | |
|---|---|---|
| Parameter | Range | Preferred Values |
| Wavelength | 680–1200 nm | 800–900, 1000–1200 nm |
| Pulse Duration | 50 µs–200 ms | 10–30 ms |
| Beam Area | >0.5 cm$^2$ | 0.75–1.0 cm$^2$ |
| Pulse Energy | 10–200 J/cm$^2$ | 30–50 J/cm$^2$ |
| Optical Coupling | external n ≧ 1.4 | n = 1.5 to 1.7 |
| Beam Convergence, At Skin Surface | collimated or convergent | f# 0.5–2 |

The inventions will now be further described with reference to the following examples.

EXAMPLES

In order to demonstrate the efficacy of the hair-removal device according to the invention, in vitro black-haired dog skin was exposed to light from the normal mode of a ruby laser at λ=694 nm with a pulse duration of 270 µs and optical fluences of 40 J/cm$^2$, 71 J/cm$^2$, and 160 J/cm$^2$. The spatial extent of the beam (8 mm diameter at the skin surface) allowed irradiation of approximately 100 hairs with a single laser shot. Following irradiation, each skin region was examined histologically. Examination revealed that at the highest fluences, dermal damage consistent with scarring of the skin was evident, indicating that at high fluence, light-induced thermal damage was not selective to the hairs. In contrast, at the lower fluences, and particularly at 40 J/cm$^2$, localized follicular damage was observed, with no noticeable damage occurring in the neighboring skin regions.

In a separate set of experiments, in order to show that the temperature increase within the irradiated hair is dependent on the degree of pigmentation, fresh human hair and skin samples having different colors were exposed using the hair-removal method described herein. The light source for all experiments was the ruby laser described above. Emitted light was first coupled into an enclosed beam-steering device containing several mirrors coated to have high reflectivities at 694 nm, and then delivered to an irradiating unit similar to that shown in FIG. 2B. The unit included a 5-cm plano-convex glass lens positioned at the proximal end of a water-cooled plexiglass housing. A sapphire contact device shaped as a 1-cm focal length lens was disposed at the distal end of the contact device, with the convex side touching the skin to allow compression during exposure as described above. Human skin was irradiated with an 8 mm diameter beam by pressing the cooled (4° C.) contact device against the skin region of the patients, and then delivering a single laser shot.

Figure 7:
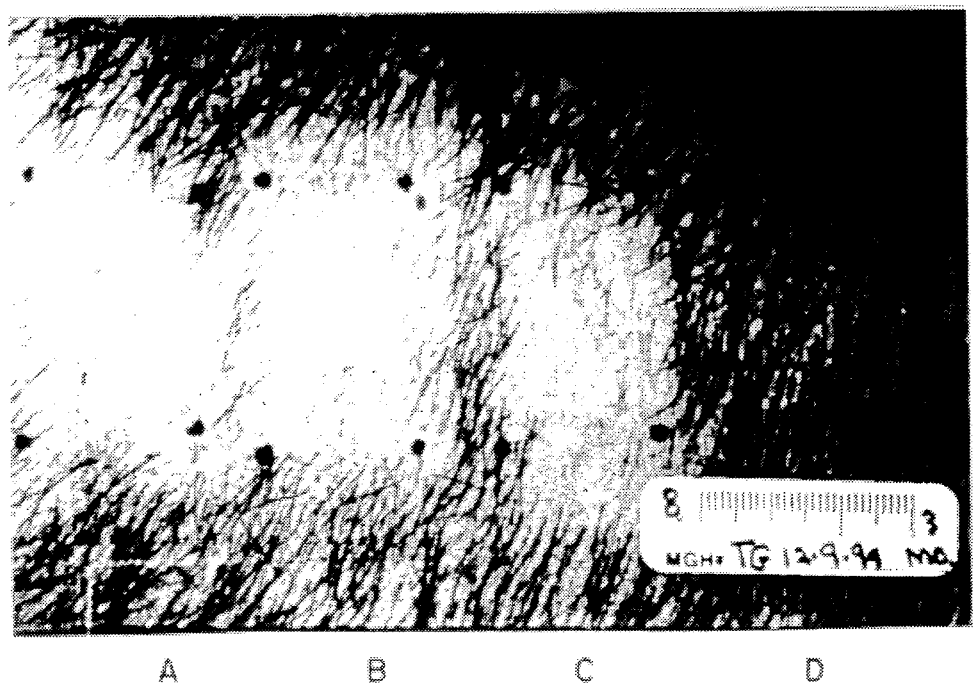
FIG. 7 is a photograph showing skin regions of a patient three months after being treated according to the hair-removal method of the invention.

The skin and hair of six adult patients having hair color ranging from red to black was irradiated and then observed. In each patient, eight treatment sites, each having an area of 10 cm$^2$, were irradiated. In order to monitor destruction of the papilla, sites 1–4 were wax-epilated prior to exposure to laser light, while sites 5–8 were shaven prior to exposure. Each site then received an optical fluence of either 28 J/cm$^2$, 42 J/cm$^2$, or 57 J/cm$^2$. Patients were seen in follow-up examinations one month after exposure. As seen from the photographs of the exposed regions shown in FIG. 7 (i.e., regions A–C), hair regrowth after three months was minimal or non-existing in all cases compared to the shaved-but-untreated region (Region D), clearly indicating permanent damage to the hair follicle. In the figure, sites A–C were treated with decreasing energy from the laser. It is clearly evident that hair removal is relatively less pronounced in region C, treated with a fluence of 28 J/cm$^2$. Region D, the control region, was shaven the same day regions A–C were treated. In addition, histological specimens obtained from the treated sites revealed that damage occurred exclusively to the hair follicle, while the surrounding dermis was essentially spared.

A separate set of experiments permitting measurement of the time-dependent temperature characteristics of hair and skin samples were conducted using a pulsed photothermal radiometry (PPTR) apparatus. In these experiments, the ruby laser described above was used at lower fluences to provide optical pulses having an energy allowing heating, but not destruction, of the follicles. Output from the laser was focussed onto the samples of human patients to provide a uniform excitation field. A New England Research, Inc. black-body radiation detector containing an amplified, liquid nitrogen-cooled HgCdTe detector was used to monitor time-dependent characteristics of the sample temperature, and a Gentec, Inc. laser energy meter was used to monitor the irradiating pulse. The output from both detectors was then amplified with a compensated 0–10 Mhz dc-coupled preamplifier, and then relayed to a digital oscilloscope for recording and storing the data.

Eight patients having various skin types and hair coloring ranging from red/blonde to black were studied. In general, the PPTR results indicated that following irradiation at 694 nm, black hair experienced a larger temperature rise than lighter brown hair, and that both of these specimens experienced higher temperature rises compared to red/blonde hair. In addition, following irradiation, type II skin had a lower temperature rise than type III or type IV skin.

Figure 8A:
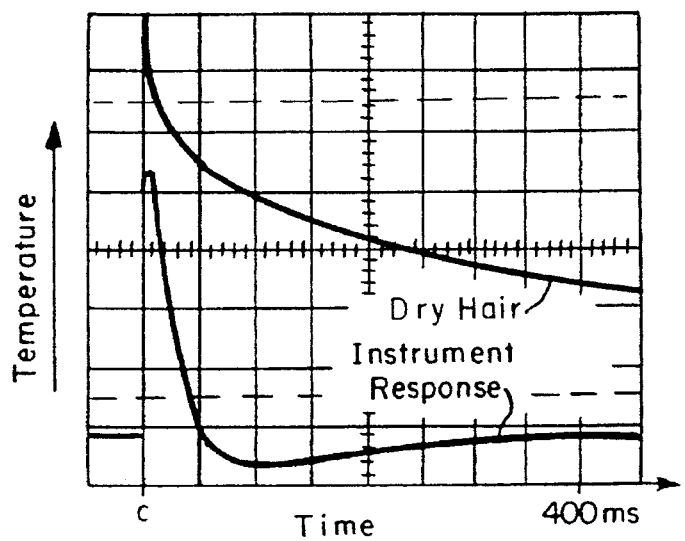
FIGS. 8A, 8B, and 8C are oscilloscope traces showing, following irradiation, the time-dependent temperature responses of, respectively, dry black hair, wet black hair, and dry skin surrounding the black hair sample; and, FIG. 9 is a plot showing the temperature rise as a function of laser pulse energy for dry hair (DH), wet hair (WH), and skin (S) samples of eight different patients.
Figure 8B:
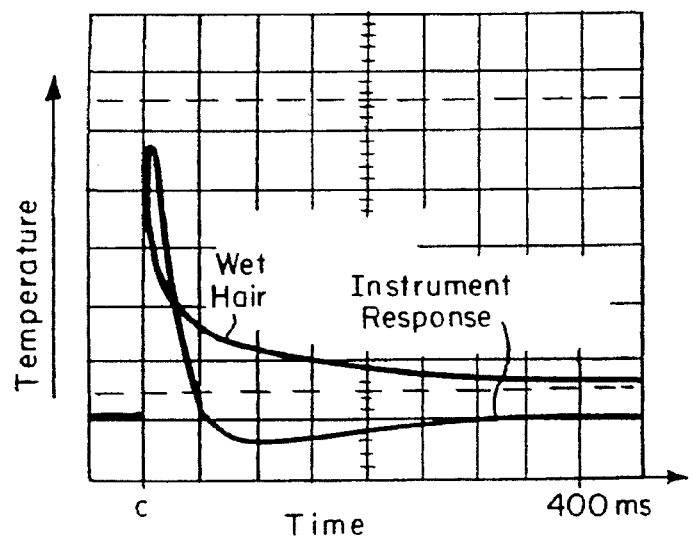
Figure 8C:
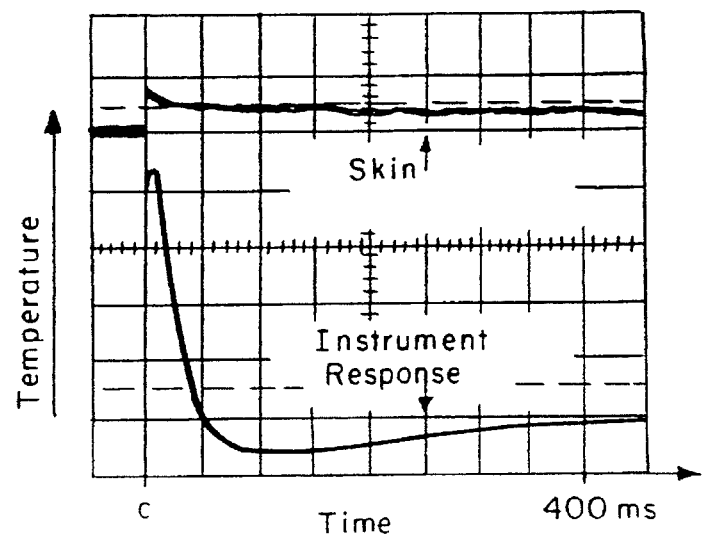

Referring now to FIGS. 8A–8C, in a particular example using a patient with black hair and white skin, time-dependent traces measured using the PPTR apparatus indicate that 400 ms after irradiation, both wet and dry black hair experience, respectively, temperature rises of about 7° C. and 72° C. (FIGS. 8A and 8B) from a baseline temperature of 23° C., whereas the surrounding skin (FIG. 8C) undergoes a temperature rise of less than 1° C. The difference in the temperature rise and time-dependent decay characteristics of the wet hair is likely due thermal effects (e.g., the higher heat capacity of wet hair).

Figure 9:
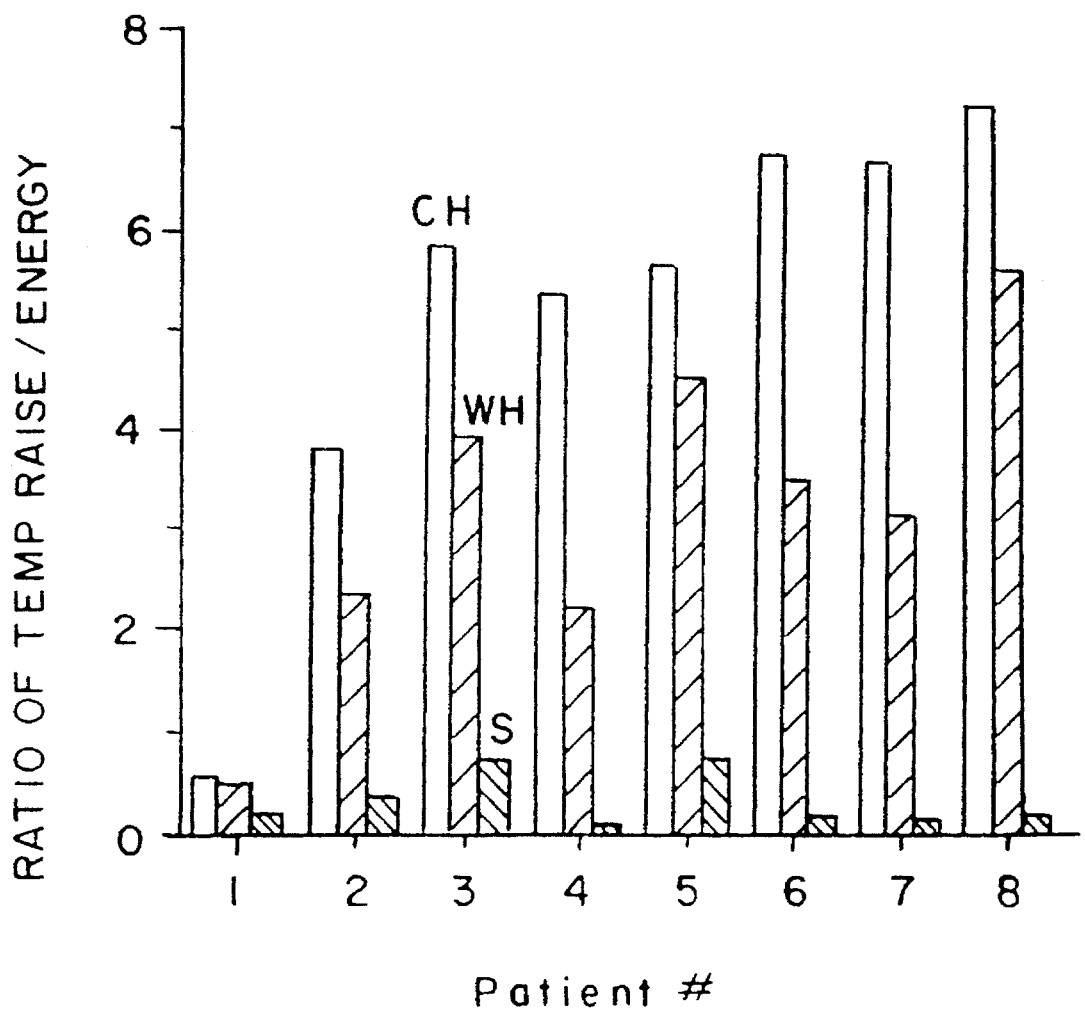

Referring now to FIG. 9, in all cases, the normalized temperature rises (i.e., the ratio of temperature rise to laser pulse energy) in the wet and dry hair follicles were significantly higher than those measured in the skin, indicating selective heating of the follicles using the method of the invention. Table 2, shown below, lists the hair and skin types of each patient in the study. The patient numbers in the table correspond to the patient numbers in FIG. 9.

TABLE 2

Patient Hair and Skin Types

| Patient | Hair | Skin Type |
|---------|------|-----------|
| 1 | Red | II |
| 2 | Brown | III |
| 3 | Brown | II |
| 4 | Gray/Black | III |
| 5 | Gray/Black | III |
| 6 | Dark Brown | III |
| 7 | Gray/Black | II |
| 8 | Black | III |

OTHER EMBODIMENTS

Other embodiments are within the scope of the following claims. For example, the contact device may not be cooled (especially when used with light-skinned patients). In addition, for certain skin types, use of an optical field having the preferred wavelength, pulse duration, spatial profile, and intensity may obviate the need for the contact device. In this case, radiation is applied directly to the region of interest after passing through the appropriate optics.

What is claimed is:

1. A method of simultaneously removing multiple hairs, each of which is in a corresponding follicle, from a skin region of a patient, said method comprising illuminating the hairs and follicles with a large-area optical radiation field delivered by a transparent device in contact with the skin region, wherein said illuminating heats the hairs and follicles so that the hairs are removed while leaving the skin region substantially free of injury.

2. The method of claim 1, wherein a substance is applied to the skin region prior to illuminating the region to facilitate the transfer of optical radiation to the hairs end follicles.

3. The method of claim 1, wherein the skin region has an epidermis layer which is in contact with said device, and wherein the device, when in contact with the, epidermis layer is cooled to a temperature below that of the skin region in order to increase the damage threshold of the epidermis layer in the skin region.

4. The method of claim 1, wherein the optical radiation is pulsed.

5. The method of claim 4, wherein the optical radiation has a pulse duration of between 10 and 30 ms.

6. The method of claim 4, wherein the radiation pulse has an energy of between 10 and 1000 J/cm$^2$.

7. The method of claim 6, wherein the radiation pulse has an energy of between 30 and 50 J/cm$^2$.

8. The method of claim 1, wherein the wavelength of the optical radiation is one which is selectively absorbed by the follicles.

9. The method of claim 8, wherein the wavelength is between 680 and 1200 nm.

10. The method of claim 9, wherein the wavelength is between 800 and 900 nm or between 1000 and 1200 nm.

11. The method of claim 1, wherein the large-area radiation field has an area of between 0.5 and 1.2 cm$^2$.

12. The method of claim 7, wherein the radiation field has an area of between 0.75 and 1 cm$^2$.

13. The method of claim 1 including applying pressure to the device, whereby the skin region in contact therewith is deformed.

14. A hair-removal device for simultaneously removing multiple hairs, each of which is in a corresponding follicle, from a skin region of a patient, comprising:

means for generating optical radiation; and an irradiating unit including a contact device comprising a large-area, optically transparent apparatus having a surface shaped to contact said skin region, said contact device receiving radiation from said means for generating and then delivering the radiation to the skin region of the patient, including the hairs and follicles in said skin region, through said surface.

15. The hair removal device of claim 14, wherein said surface is convex.

16. The hair-removal device of claim 15, wherein said contact device includes a lens.

17. The hair removal device of claim 15 wherein said apparatus is applied to the skin region under pressure, whereby the skin region is deformed to bring at least most of said convex surface into contact with said skin region.

18. The hair-removal device of claim 14, wherein said optically transparent apparatus comprises material selected from the group consisting of sapphire, fused quartz, fused silica, polymeric materials, and glass.

19. The hair-removal device of claim 18, wherein said optically transparent material has a refractive index substantially matched to that of the skin region.

20. The hair-removal device of claim 19, wherein said material is sapphire.

21. The hair removal device of claim 14 including means for cooling the surface of the optically transparent apparatus in contact with said skin region to a temperature below that of the skin region.

22. The hair removal device of claim 21 wherein said means for cooling includes means for passing cooled water through said apparatus near said surface.

* * * * *

(12) EX PARTE REEXAMINATION CERTIFICATE (7161st)
United States Patent
Anderson et al.

(10) Number: US 5,595,568 C1
(45) Certificate Issued: Nov. 17, 2009

(54) PERMANENT HAIR REMOVAL USING OPTICAL PULSES

(75) Inventors: R. Rox Anderson, Lexington, MA (US); Melanie Grossman, Boston, MA (US); William Farinelli, Danvers, MA (US)

(73) Assignee: The General Hospital Corporation

Reexamination Request:
No. 90/009,217, Jul. 10, 2008
No. 90/009,355, Dec. 8, 2008

Reexamination Certificate for:
Patent No.: 5,595,568
Issued: Jan. 21, 1997
Appl. No.: 08/382,122
Filed: Feb. 1, 1995

(51) Int. Cl.
*A61B 18/20* (2006.01)
*A61B 17/30* (2006.01)
*A61B 17/22* (2006.01)
*A61B 18/00* (2006.01)
*A61B 18/22* (2006.01)
*A61B 17/00* (2006.01)
*A61N 5/06* (2006.01)

(52) U.S. Cl. .................................................. 606/9
(58) Field of Classification Search .................. None
See application file for complete search history.

(56) References Cited

U.S. PATENT DOCUMENTS

| | | |
|---|---|---|
| 2,262,215 A | 11/1941 | Bird |
| 3,404,350 A | 10/1968 | Muncheryan |
| 3,538,919 A | 11/1970 | Meyer |
| 3,583,919 A | 6/1971 | Meyer |
| 3,693,623 A | 9/1972 | Harte et al. |
| 3,821,510 A | 6/1974 | Muncheryan |
| 3,834,391 A | 9/1974 | Block |
| 3,900,034 A | 8/1975 | Katz et al. |
| 3,916,143 A | 10/1975 | Farrell |
| 4,140,130 A | 2/1979 | Storm, III |
| 4,174,713 A | 11/1979 | Mehl |
| 4,174,714 A | 11/1979 | Mehl |
| 4,388,924 A | 6/1983 | Weissman et al. |
| 4,461,294 A | 7/1984 | Baron |
| 4,566,454 A | 1/1986 | Mehl et al. |
| 4,608,978 A | 9/1986 | Rohr |
| 4,617,926 A | 10/1986 | Sutton et al. |
| 4,718,416 A | 1/1988 | Nanaumi et al. |
| 4,733,660 A | 3/1988 | Itzkan |
| 4,819,669 A | 4/1989 | Politzer et al. |
| 4,829,262 A | 5/1989 | Furumoto |
| 4,930,504 A | 6/1990 | Diamantopoulos et al. |
| 5,000,752 A | 3/1991 | Hoskin et al. |
| 5,057,104 A | 10/1991 | Chess |
| 5,059,192 A | 10/1991 | Zaias |

(Continued)

FOREIGN PATENT DOCUMENTS

| | | |
|---|---|---|
| CA | 2210720 | 8/1996 |
| CN | 86201325 U | 11/1987 |
| DE | 3220962 | 12/1983 |
| DE | 4304091 | 8/1994 |
| DE | 19512481 | 10/1995 |
| EP | 0142671 | 5/1985 |
| EP | 0292621 | 11/1988 |

(Continued)

OTHER PUBLICATIONS

U.S. Appl. No. 08/280,928, Tankovich.
File History, U.S. Appl. No. 08/280,928, entitled "Hair Removal Method", filed Jul. 26, 1994, now abandoned.

(Continued)

*Primary Examiner*—David O. Reip

(57) ABSTRACT

A method and apparatus for simultaneously removing multiple hair follicles from a skin region of a patient. The method includes the step of illuminating the hair follicles with a large-area, optical radiation field by way of a transparent contact device proximal to the skin region. This allows portions of the hair follicles to be heated and then removed, while the surrounding skin region is left relatively free of injury.

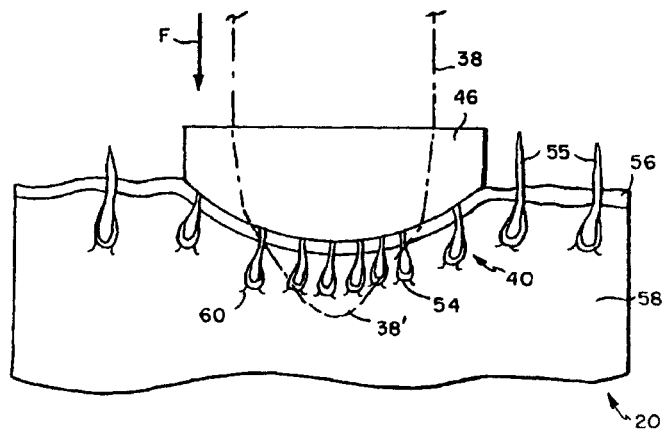

U.S. PATENT DOCUMENTS

| | | |
|---|---|---|
| 5,065,515 A | 11/1991 | Iderosa |
| 5,139,495 A | 8/1992 | Daikuzono et al. |
| 5,182,857 A | 2/1993 | Simon et al. |
| 5,217,455 A | 6/1993 | Tan |
| 5,226,907 A | 7/1993 | Tankovich |
| 5,282,797 A | 2/1994 | Chess |
| 5,290,273 A | 3/1994 | Tan |
| 5,290,274 A | 3/1994 | Levy et al. |
| 5,299,104 A | 3/1994 | Parmentier |
| 5,299,453 A | 4/1994 | Sprunt et al. |
| 5,304,170 A | 4/1994 | Green |
| 5,312,395 A | 5/1994 | Tan et al. |
| 5,320,618 A | 6/1994 | Gustafsson et al. |
| 5,337,741 A | 8/1994 | Diamond |
| 5,344,418 A | 9/1994 | Ghaffari |
| 5,397,327 A | 3/1995 | Koop et al. |
| 5,405,368 A | 4/1995 | Eckhouse et al. |
| 5,425,728 A | 6/1995 | Tankovich |
| 5,464,436 A | 11/1995 | Smith |
| 5,474,549 A | 12/1995 | Ortiz et al. |
| 5,486,172 A | 1/1996 | Chess |
| 5,522,813 A | 6/1996 | Trelles et al. |
| 5,527,350 A | 6/1996 | Grove et al. |
| 5,546,214 A | 8/1996 | Black et al. |
| 5,554,156 A | 9/1996 | Shimizu et al. |
| 5,586,981 A | 12/1996 | Hu |
| 5,595,568 A | 1/1997 | Anderson et al. |
| 5,606,798 A | 3/1997 | Kelman et al. |
| 5,620,478 A | 4/1997 | Eckhouse et al. |
| 5,630,811 A | 5/1997 | Miller |
| 5,647,866 A | 7/1997 | Zaias et al. |
| 5,653,706 A | 8/1997 | Zavislan et al. |
| 5,683,380 A | 11/1997 | Eckhouse et al. |
| 5,707,403 A | 1/1998 | Grove et al. |
| 5,735,844 A | 4/1998 | Anderson et al. |
| 5,752,948 A | 5/1998 | Tankovich et al. |
| 5,757,949 A | 5/1998 | Kinoshita et al. |
| 5,766,214 A | 6/1998 | Mehl, Sr. et al. |
| 5,814,040 A | 9/1998 | Nelson et al. |
| 5,817,089 A | 10/1998 | Tankovich et al. |
| 5,820,625 A | 10/1998 | Izawa et al. |
| 5,824,023 A | 10/1998 | Anderson |
| 5,836,938 A | 11/1998 | Slatkine et al. |
| 5,846,252 A | 12/1998 | Mehl, Sr. |
| 5,853,407 A | 12/1998 | Miller |
| 5,860,967 A | 1/1999 | Zavislan et al. |
| 5,868,732 A | 2/1999 | Waldman et al. |
| 5,871,479 A | 2/1999 | Furumoto et al. |
| 5,879,346 A | 3/1999 | Waldman et al. |
| 5,885,273 A | 3/1999 | Eckhouse et al. |
| 5,906,610 A | 5/1999 | Mehl, Sr. et al. |
| 5,916,211 A | 6/1999 | Quon et al. |
| 5,925,035 A | 7/1999 | Tankovich |
| 5,989,267 A | 11/1999 | Anderson |
| 6,015,404 A | 1/2000 | Altshuler et al. |
| 6,036,684 A | 3/2000 | Tankovich et al. |
| 6,045,548 A | 4/2000 | Furumoto et al. |
| 6,050,990 A | 4/2000 | Tankovich et al. |
| 6,063,074 A | 5/2000 | Tankovich |
| 6,063,076 A | 5/2000 | Mehl, Sr. et al. |
| 6,080,147 A | 6/2000 | Tobinick |
| 6,090,101 A | 7/2000 | Quon et al. |
| 6,143,287 A | 11/2000 | Ben-Hur et al. |
| 6,149,644 A | 11/2000 | Xie |
| 6,149,645 A | 11/2000 | Tobinick |
| 6,152,917 A | 11/2000 | Tankovich |
| 6,165,171 A | 12/2000 | Tobinick |
| 6,168,589 B1 | 1/2001 | Tobinick |
| 6,168,590 B1 | 1/2001 | Neev |
| 6,210,402 B1 | 4/2001 | Olsen et al. |
| 6,214,034 B1 | 4/2001 | Azar et al. |
| 6,217,572 B1 | 4/2001 | Tobinick |
| 6,228,075 B1 | 5/2001 | Furumoto |
| 6,228,078 B1 | 5/2001 | Eggers et al. |
| 6,235,015 B1 | 5/2001 | Mead, III et al. |
| 6,248,102 B1 | 6/2001 | Stewart |
| 6,267,755 B1 | 7/2001 | Clementi et al. |
| 6,267,771 B1 | 7/2001 | Tankovich et al. |
| 6,273,883 B1 | 8/2001 | Furumoto |
| 6,273,884 B1 | 8/2001 | Altshuler et al. |
| 6,277,111 B1 | 8/2001 | Clement et al. |
| 6,280,438 B1 | 8/2001 | Eckhouse et al. |
| 6,283,956 B1 | 9/2001 | McDaniel |
| 6,287,549 B1 | 9/2001 | Sumian et al. |
| 6,365,145 B1 | 4/2002 | Ben-Hur et al. |
| 6,383,176 B1 | 5/2002 | Connors et al. |
| 6,485,484 B1 | 11/2002 | Connors et al. |
| 6,508,813 B1 | 1/2003 | Altshuler |
| 6,511,475 B1 | 1/2003 | Altshuler et al. |
| 6,514,242 B1 | 2/2003 | Vasily et al. |
| 6,514,243 B1 | 2/2003 | Eckhouse et al. |
| 6,547,781 B1 | 4/2003 | Furumoto |
| 6,595,985 B1 | 7/2003 | Tobinick |
| 6,610,052 B2 | 8/2003 | Furumoto |
| 6,632,218 B1 | 10/2003 | Furumoto et al. |
| 6,706,035 B2 | 3/2004 | Cense et al. |
| 7,029,469 B2 | 4/2006 | Vasily |

FOREIGN PATENT DOCUMENTS

| | | |
|---|---|---|
| EP | 0565331 | 10/1993 |
| EP | 0575274 | 12/1993 |
| EP | 0 601 130 | 6/1994 |
| EP | 0 685 180 | 12/1995 |
| EP | 0736308 | 10/1996 |
| EP | 0806913 | 11/1997 |
| EP | 0893140 | 1/1999 |
| EP | 1123900 | 8/2001 |
| EP | 1219258 | 7/2002 |
| FR | 2199453 | 4/1974 |
| FR | 2590791 | 6/1987 |
| FR | 2591902 | 6/1987 |
| GB | 2123287 | 2/1984 |
| IL | 0086872 | 11/1988 |
| IL | 0103728 | 4/1993 |
| IL | 0097531 | 12/1995 |
| JP | 64-080309 | 3/1989 |
| JP | 199574 | 4/1989 |
| JP | 1181877 | 7/1989 |
| JP | 2-13014 | 4/1990 |
| JP | 2159207 | 6/1990 |
| JP | 3123544 | 5/1991 |
| JP | 03-193003 | 8/1991 |
| JP | 3218742 | 9/1991 |
| JP | 04-067860 | 3/1992 |
| JP | 4-322668 | 11/1992 |
| JP | 5-329218 | 12/1993 |
| JP | 6509734 | 11/1994 |
| WO | WO-86/02783 | 5/1986 |
| WO | WO-89/00027 | 1/1989 |
| WO | WO-92/13684 | 8/1992 |
| WO | WO-92/16338 | 10/1992 |
| WO | WO-92/19165 | 11/1992 |
| WO | WO-93/05920 | 4/1993 |
| WO | WO-93/08715 | 5/1993 |
| WO | WO-95/15725 | 6/1995 |
| WO | WO-96/23447 | 8/1996 |
| WO | WO-96/41579 | 12/1996 |
| WO | WO-2005/016453 | 2/2005 |
| WO | WO-2006/076554 | 7/2006 |
| ZA | 9500073 A | 9/1995 |

OTHER PUBLICATIONS

File History U.S. Pat. No. 5,683,380, entitled "Method and Apparatus for Depilation Using Pulsed Electromagnetic Radiation", filed Mar. 29, 1995, issued Nov. 4, 1997.
"Basic Principles: Microanatomy of the Skin; Derivatives of the Skin; Physiology of the Skin; Biochemistry of the Skin; Immunology of the Skin; Terminology of Skin Lesions; Examining the Skin; Basics of Medical Therapy".
"U.S. Health Care Industry Gears Up to 'Cure' Soviet Health Care Woes—Includes Text of Joint Statement on the Fourth Session of the Joint U.S.—USSR Commercial Commission Working Group on Medical Products and Supplies", Business America, Jul. 2, 1990, http://findarticles.com/p/articles/mi_m1052/is_n13_vIII/ai_9154083, printed Apr. 5, 2007.
Adams, et al., "The Effect of Wavelength, Power and Treatment Pattern on the Outcome of Laser Treatment of Port–Wine Stains", British Journal of Dermatology, 117:487–494 (1987).
Alster, et al., "Comparison of Four Carbon Dioxide Resurfacing Lasers. A Clinical and Histopathologic Evaluation", Dermatol Surg., 25(3):153–158 (1999) Abstract Only.
Altshuler, et al., "Extended Theory of Selective Photothermolysis", Lasers in Surgery and Medicine, 29:416–432 (2001).
Altshuler, et al., "Optical Properties of Human Hair", Proc. SPIE, 2323:344–350 (1995).
Anderson, et al., "Lasers in Dermatology Provide a Model for Exploring New Applications in Surgical Oncology", International Advances in Surgical Oncology, 5:341–358 (1982).
Anderson, et al., "Selective Photothermolysis of Cutaneous Pigmentation by Q–Switched Nd:YAG Laser Pulses at 1064, 532, and 355 nm", Journal of Investigative Dermatology, 93(1):28–32 (1989).
Anderson, et al., "Selective Photothermolysis: Precise Microsurgery by Selective Absorption of Pulsed Radiation", Science, 220:524–527 (1983).
Anderson, et al., "The Optics of Human Skin", Journal of Investigative Dermatology, 77(1):13–19 (1981).
Astore, et al., "The Normal Trichogram of Pubic Hair", British Journal of Dermatology, 101:441–444 (1979).
Awan, "Argon Laser Treatment of Trichiasis", Ophthalmic Surgery, 17(10):658–660 (1986).
Basic Laser Physics and Visible Light Laser Surgery, pp. 1021–1022.
Berlien, et al., "Lasers in Pediatric Surgery", Progress in Pediatric Surgery, 25:5–22 (1990).
Bernstein, et al., "Scar Resurfacing with High–Energy, Short–Pulsed and Flashscanning Carbon Dioxide Lasers", Dermatol. Surg., 24(1):101–107 (1998) Abstract Only.
Boergen, et al., "Experimental Studies on Argon Laser Coagulation of Small Blood Vessels", Mod. Probl. Opthal., 20:174–183 (1979).
Buckley, et al., "Reflection Spectrophotometry. III. Absorption Characteristics and Color of Human Skin", Archives of Dermatology, 89:170–176 (1964).
Campbell, "Thermoablation Treatment for Trichiasis Using the Argon Laser", Australian and New Zealand Journal of Ophthalmology, 18(4):427–430 (1990).
Chernoff, et al., "Silk Touch: A New Technology for Skin Resurfacing in Aesthetic Surgery", J. Clin. Laser Med. Surg., 13(2):97–100 (1995) Abstract Only.

Dierickx, et al., "Thermal Relaxation of Port–Wine Stain Vessels Probed In Vivo: The Need for 1–10 Millisecond Laser Pulse Treatment", Journal of Investigative Dermatology, 105(5):709–714 (1995).
Dixon, et al., "Argon and Neodymium YAG Laser Therapy of Dark Nodular Port Wine Stains in Older Patients", Lasers in Surgery and Medicine, 6:5–11 (1986).
Dover, et al., Illustrated Cutaneous Laser Surgery: A Practitioners Guide, Appleton & Lange, Norwalk, CT, pp. 14–18 (1990).
Dreno, et al., "The Benefit of Chilling in Argon–Laser Treatment of Port–Wine Stains", Plastic and Reconstructive Surgery, 75(1):42–45 (1985).
Ebling, "Chapter 19: Biology of Hair Follicles", *Dermatology in General Medicine, Textbook and Atlas*, Third Edition, McGraw–Hill, pp. 213–219.
Ehlers, et al., "Cytophotometrische Untersuchungen zur Frage der Cancerogenen Wirkung von Rubinlaser–Licht", Der Hautarzt, 24:423–430 (1973) German Language.
Ehlers, et al., "Zur Frage der Kanzerogenen Wirkung von Rubinlaserstrahlen", Med. Klin, 68:1229–1238 (1973) English Abstract.
Finkelstein, et al., "Epilation of Hair–Bearing Urethral Grafts Using the Neodymium:YAG Surgical Laser", Journal of Urology, 146:840–842 (1991).
Finkelstein, et al., "Epilation of Hair–Bearing Urethral Grafts Utilizing the Neodymium:YAG Surgical Laser", Lasers in Surgery and Medicine, 10:189–193 (1990).
Gilchrest, et al., Chilling Port Wine Stains Improves the Response to Argon Laser Therapy, Plastic and Reconstructive Surgery, 69(2):278–283 (1982).
Goldman, "A Status on Laser Surgery", Contemporary Surgery, 3(2):18–24 (1973).
Goldman, "Chapter Eleven: Laser Techniques in Various Medical Specialties", *Laser Non–Surgical Medicine: New Challenges for an Old Application*, Technomic Publishing, Inc., pp. 213–238 (1991).
Goldman, "Comparison of the Biomedical Effects of the Exposure of Human Tissues to Low and High Energy Lasers", Annals New York Academy of Sciences, pp. 802–829 (1965).
Goldman, "Dermatologic Manifestations of Laser Radiation", Proceedings of the First Annual Conference on Biological Effects of Laser Radiation, Washington, DC, Federation of American Societies for Experimental Biology, Suppl. 14:92–93 (1965).
Goldman, "Effects of New Laser Systems of the Skin", Arch Dermatol., 108:385–390 (1973).
Goldman, "Laser Action at the Cellular Level", JAMA, 198(6):173–176 (1966).
Goldman, "Laser Surgery for Skin Cancer", New York State Journal of Medicine, Oct., pp. 1897–1900 (1977).
Goldman, "The Skin", Arch. Environ Health, 18:434–436 (1969).
Goldman, *Biomedical Aspects of the Laser*, Springer–Verlag, New York, Inc., pp. 9–21; 72–76; 96–97; 119–137; 168–182 (1967).
Goldman, et al., "Treatment of Basal Cell Epithelioma by Laser Radiation", JAMA, 189(10):171–173 (1964).
Goldman, et al., "Effect of the Laser Beam on the Skin—Preliminary Report", Journal of Investigative Dermatology, 40:121–122 (1963).
Goldman, et al., "Impact of the Laser on Nevi and Menalomas", Arahc Dermatol., 90:71–75 (1964).

Goldman, et al., "Investigative Studies with Quartz Rods for High Energy Laser Transmission", Medical Research Engineering, Fourth Quarter, pp. 12–17 (1967).

Goldman, et al., "Laser Surgery of Angiomas with Special Reference to Port–Wine Angiomas", XIII International Congress of Dermatology, Munich, Jul. 31–Aug. 5, 1967, vol. 2, Springer–Verlag, pp. 1388–1390 (1968).

Goldman, et al., "Laser Treatment of Tattoos: A Preliminary Study of Three Year's Clinical Experience", JAMA, 201(11):841–844 (1967).

Goldman, et al., "Long–Term Laser Exposure of a Senile Freckle", Arch Environ Health, 22:401–403 (1871).

Goldman, et al., "Pathology of the Effect of the Laser Beam on the Skin", Nature, 197:912–914 (1963).

Goldman, et al., "Preliminary Investigation of Fat Embolization from Pulsed Ruby Laser Impacts of Bone", Nature, 221:361–363 (1969).

Goldman, et al., "Radiation from a Q–Switched Ruby Laser", JID, 44:69–71 (1965).

Goldman, et al., "Replica Microscopy and Scanning Electron Microscopy of Laser Impacts on the Skin", Journal of Investigative Dermatology, 52(1):18–24 (1969).

Goldman, et al., "The Biomedical Aspects of Lasers", JAMA, 188(3):230–234 (1964).

Goldman, et al., "The Effect of Repeated Exposures to Laser Beams", Acta Derm. Venereol., 44:264–267 (1964).

Goldman, et al., Lasers in Medicine, (Goldman and Rockwell, eds.), Gordon and Breach, Science Publishers, Inc., pp. 259, 264, 265, 317, 366, 367 (1971).

Goldman, M., et al., "Treatment of Benign Pigmented Cutaneous Lesions", *Cutaneous Laser Surgery*, pp. 106–141 (1994).

Goldman, m., et al., "Laser Skin Resurfacing of the Face with a Combined CO2/Er:YAG Laser", Dermatol. Surg., 26(2):102–104 (2000) Abstract Only.

Gossman, et al., "Experimental Comparison of Laser Cryosurgical Cilia Destruction", Ophthalmic Surgery, 23(3):179–182 (1992).

Gossman, et al., "Prospective Evaluation of the Argon Laser in the Treatment of Trichiasis", Ophthalmic Surgery, 23(3):183–187 (1992).

Grossman, "Laser Targeted at Hair Follicles", American Society for Laser Medicine and Surgery Abstracts, No. 221 Abstract Only.

Grossman, et al., "Damage to Hair Follicles by Normal–Mode Ruby Laser Pulses", Journal of the American Academy of Dermatology, 35(6):889–894 (1996).

Haina, et al., "Possibilities for the Increase of the Coagulation Depth in Skin with the Argonlaser", Laser Optoelectronics in Medicine: Proceedings of the 7th Congress International Society for Laser Surgery and Medicine in Connection with Laser 87 Optoelectronics, (Waidelich, et al., eds.), pp. 539–542 (1988).

Hayashi, et al. "Q–Switched Ruby Laser Treatment of Ota's Neuvs", UJ. Jpn. P.R.S., 13:705–714 (1993).

Hayes, et al., "Thermal Model for Retinal Damage Induced by Pulsed Lasers", Aerospace Medicine, 39(5):474–480 (1968).

Hedelund, et al., "CO2 Laser–Resurfacing: Increased Risk of Side Effects After UV–Exposure—An Experimental Animal Study", Lasers Surg. Med., 36(2):79–84 (2005).

Henderson, et al., "The 'light–touch': a Dermatology Handpiece Designed to Improve the Efficacy and Safety of Laser Treatment of Port–Wine Stains", Phys. Med. Biol., 32(12):1627–1630 (1987).

Ho, et al., "Laser Resurfacing in Pigmented Skin", Dermatol. Surg, 21(12): 1035–1037 (1995) Abstract Only.

Huerter, et al., "Multiple Eruptive Vellus Hair Cysts Treated with Carbon Dioxide Laser Vaporization", Determol. Surg. Oncol., 13.3:260–263 (1987).

Jacques, "Laser–Tissue Interactions", Lasers in General Surgery, 72(3):531–558 (1992).

Khatri, et al., "Comparison of Erbium: YAG and Carbon Dioxide Lasers in Resurfacing of Facial Rhytides", Arch. Dermatol., 135(4):391–397 (1999) Abstract Only.

Kim, et al., "Regrowth of Grafted Human Scalp Hair after Removal of the Bulb", Dermatol. Surg., 21:312–313 (1995).

Kincade, "First Laser Hair–Removal System Gains FDA Clearance", Laser Focus World, 31(6):36, 38 (1995).

Kincade, "New Procedures Push Tissue Studies Beneath the Surface", Laser Focus World, Aug., pp. 57–63 (1995).

Kuhns, et al., "Laser Injury in Skin", Laboratory Investigation, 17(1):1–13 (1967).

Kuriloff, et al. "Pharyngoesophoageal Hair Growth: The Role of Laser Epilation", Case Reports, 98(4): 342–345 (1988).

Lage, et al., "The Pathology of Laser Irradation of the Skin and Body Wall of the Mouse", Laser Irradiation, 47(4):643–663 (1965).

Landthaler, et al. "Neodymium–YAG Laser for Vascular Lesions", Journal of the American Academy of Dermatology, 14(1):107–117 (1986).

Lask, et al., "Laser Skin Resurfacing with the SilkTouch Flashscanner for Facial Rhytides", Dermatol. Surg., 21(12):1021–1024 (1995) Abstract Only.

Lask, et al., "Neodymium:Yttrium–Aluminum–Garnet Laser for the Treatment of Cutaneous Lesions", Clinics in Dermatology, 13:81–86 (1995).

Maiman, "A Look at Things to Com: Biomedical Lasers Evolve Toward Clinical Applications", Hospital Management, Apr. pp. 39–41 (1966).

Matsumoto, et al., "Ruby Laser Treatment of Melanin Pigmented Skin Lesions using Toshiba Model LRT–301A Ruby Laser", Department of Plastic Surgery School of Medicine, Hokkaido University, 10(3):451–454 (1989) English Translation.

Mckenzie, "Physics of Thermal Processes in Laser–Tissue Interaction", Phys. Med. Biol., 35(9):1175–1209 (1990).

Meloy, "The Laser's Bright Magic", National Geographic, Dec., pp. 858–881, (1966).

Mester, et al., "The Biomedical Effects of Laser Application", Lasers in Surgery and Medicine, 5:31–39 (1985).

Mester, et al.,. "The Effect of Laser Radiation on Hair Growth of the Mouse", Radiobiologia Radiotherapin, 9(5):621–626 (1968) English Translation.

Mester, et al., "Untersuchungen uber die hemmende bzw. fordemde Wirkung der Laserstrahlen", Langenbecks Arden fuer Chirurgie, 322:1022–1027 (19650 English Abstract.

Miyasaka, et al., "Basic and Clinical Studies of Laser for Hyperpigmented Skin Lesions", pp. 117–127 (1991).

Moy, et al., "Skin Resurfacing of Facial Rhytides and Scars with the 90–microsecond short pulse CO2 Laser. Comparison to the 900–microsecond dwell time CO2 Lasers and Clinical Experience", Dermatol. Surg., 24(12):1390–1396 (1998) Abstract Only.

Nakaoka, et al., "The Square and Uniform Intensity Ruby Laser for the Treatment of Pigmented Skin Lesions", Eur J. Plast. Surg., 15:23–30 (1992).

Nelson, et al., "'Dynamic' Cooling of the Epidermis During Laser Port Wine Stain Therapy", American Society for Laser Medicine and Surgery Abstracts, No. 253, Abstract Only.

Nelson, et al., "Dynamic Epidermal Cooling During Pulsed Laser Treatment of Port–Wine Stain", Arch Dermatol, 131:695–700 (1995).

Ohshiro, et al., "The Ruby and Argon Lasers in the Treatment of Naevi", Annals Academy of Medicine, 12(2):388–395 (1983).

Ohshiro, et al., Laser Treatment for Naevi, John Wiley & Sons, pp. 166–191, 195–201 (1995).

Ohtsuka, et al., "Ru Laser: Histological Studies and Clinical Experiences of Ruby Laser Treatment", 11(4):107–115 (1991) English Abstract.

Oliver, "Dermal–Epidermal Interactions and Hair Growth", Journal of Investigative Dermatology, 96:76s (1991).

Ono, et al., "Histopathological Alteration of Skin after Irradiation of Ruby Laser", 11(4):99–105 (1991).

Oshry, et al., "Argon Green Laser Photoepilation in the Treatment of Trachomatous Trichlasis", Ophthalmic Plastic and Reconstructive Surgery, 10(4):253–255 (1994).

Parrish, et al., "Selective Thermal Effects with Pulsed Irradiation from Lasers: From Organ to Organelle", The Journal of Investigative Dermatology, 80(6):75s–80s (1983).

Paul, et al., "The Effect of Temperature and Other Factors on Selective Microvascular Damage Caused by Pulsed Dye Laser", Journal of Investigative Dermatology, 81(4):333–336 (1983).

Philipp, et al., "Ten Years of Laser Treatment of Congenital Vascular Disorders", SPIE, 2327:44–53 (1994).

Polla, et al., "Melanosomes Are a Primary Target of Q–Switched Ruby Laser Irradiation in Guinea Pig Skin", Journal of Investigative Dermatology, 89(3):281–286 (1987).

Random House Webster's College Dictionary, pp. 286, 425, 1044 (1999).

Riggle, et al, "Chapter 3: Laser Effects on Normal and Tumor Tissue", *Laser Applications in Medicine and Biology*, pp. 38–65 (1970).

Rosenfeld, et al., "The Treatment of Cutaneous Vascular Lesions with the Nd:YAG Laser", Annals of Plastic Surgery, 21(3):223–230 (1988).

Rosenfeld, et al., "Treatment of Cutaneous and Deep Vascular Lesions with the Nd:YAG Laser", Lasers in Surgery and Medicine, 6:20–23 (1986).

Ross, et al. "Long–Term Results after CO2 Laser Skin Resurfacing: A Comparison of Scanned and Pulsed Systems", J. Am. Acad. Dermatol., 37(5 Pt 1):709–718 (1997) Abstract Only.

Schrimer, "Simultaneous Thermal and Optical Breakdown Mode Dual Laser Action", Ophthalmologica, 205:169–177 (1992).

Shapshay, et al., "Neodymium–YAG Laser Photocoagulation of Hemangiomas of the Head and Neck", Laryngoscope, 97:323–330 (1987).

Sheblakov, et al., "New Applications for the YAG–ND Laser in Medicine", Proceedings of the 2nd School of Young Scientists of the General Physics Institute of Russia, Moscow, p. 20 (1989) English Translation.

Sheblakov, et al., "Novel Use of Nd:YAG Laser in Medicine", Methods of Modern Optics in General Physics Problems Solution, Scientific Proceedings, p. 20 (1989) English Translation.

Sherwood, et al., "Effect of Wavelength of Cutaneous Pigment Using Pulsed Irradiation", Journal of Investigative Dermatology, 92(6):717–720 (1989).

Shimbashi, et al., "Ruby Laser Treatment of Pigmented Skin Lesions", Aesth. Plast. Surg., 19:225–229 (1995).

Shimizu, et al., "Ruby Laser and Its Medical Applications", 45(4):353–355 (1990).

Solomon, et al., "Histopathology of the Laser Treatment of Port–Wine Lesions", Journal of Investigative Dermatology, 50(2):141–146 (1968).

Stedman's Medical Dictionary, Twenty–Third Edition, p. 203 (1976).

Supraherent Industries, Ltd., "LadyLaze" Information downloaded from http://web.archive.org/web/19961109160641/www.linkcafe.co.uk/business/supraherent/set.html.

Tan, et al., "Laser Therapy for Selected Cutaneous Vascular Lesions in the Pediatric Population: A Review", Pediatrics, 82(4):652–662 (1988).

Tan, et al., "Treatment of Children with Port–Wine Stains Using the Flashlamp–Pulsed Tunable Dye Laser", NEJM, 320(7):416–421 (1989).

Tanino, et al., "Development of Ruby Laser System for Medical Use", Journal of the Japanese Society for Laser Surgery and Medicine, 11(4):93–99 (1991) English Translation.

Taylor, et al. "Treatment of Tattoos by Q–Switched Ruby Laser", Arch Dermatol, 126:893–899 (1990).

The American Heritage Dictionary, Office Edition, Third Edition, pp. 191, 249 (1994).

The American Heritage Dictionary, Second College Edition, pp. 121, 315 (1985).

Trelles, et al., "A Clinical and Histological Comparison of Flashscanning Versus Pulsed Technology in Carbon Dioxide Laser Facial Skin Resurfacing", Dermatol. Surg.,. 24(1):43–49 (1998) Abstract Only.

Trelles, et al., "Penetration Depth of Ultrapulse Carbon Dioxide Laser in Human Skin", Dermatol. Surg., 22:863–865 (1996).

Van Gemert, et al., "A Model Approach to Laser Coagulation of Dermal Vascular Lesions", Arch Dermatol Res, 270:429–439 (1981).

Van Gemert, et al., "Is There An Optimal Laser Treatment for Port Wine Stains", Lasers in Surgery and Medicine, 6:76–83 (1986).

Van Germert, et al., "Time Constants in Thermal Laser Medicine", Lasers in Surgery and Medicine, 9:405–421 (1989).

Van Gemert, et al., "Treatment of Port–Wine Stains; Analysis", Medical Instrumentation, 21(4):213–217 (1987).

Watanabe, et al., "Comparative Studies of Femtosecond to Microsecond Laser Pulses on Selective Pigmented Cell Injury in Skin", Photochemistry and Photobiology, pp. 757–762 (1991).

Watanabe, et al., "The Effect of Pulse Duration on Selective Pigmented Cell Injury by Dye Lasers", Abstracts, 88(4):523 (1987) Abstract only.

Welch, et al., "Evaluation of Cooling Techniques for the Protection of the Epidermis During ND–YAG Laser Irridiation of the Skin", Neodymium–YAG Laser in Medicine and Surgery (Joffe, et al., eds.), Elsevier Science Publishing, Inc., pp. 196–204 (1983).

Werner, et al., Treatment of Haemungiemas with Neodymium:YAG Laser (Nd:YAG Laser), Laryngo–Rhino–Otol, 71:388–395 (1992) English Translation.

Wheeland, "Clinical Uses of Lasers in Dermatology", Lasers in Surgery and Medicine, 16:2–23 (1995).

Wheeland, "Microanatomy and Physiology of the Skin".

Yules, et al., "The Effect of Q–Switched Ruby Laser Radiation of Dermal Tattoo Pitment in Man", Arch Surg, 95:179–180 (1967).

Anvari, et al., "A Theoretical Study of the Thermal Response of Skin to Cryogen Spray Cooling and Pulsed Laser Irradiation: Implications for Treatment of Port Wine Stain Birthmarks", Phys. Med. Biol. 40:1451–1465 (1995).

Article regarding Soviet–American Symposium on Research Technology and Trade, dated Jan. 22, 1991, Exhibit 10 to Tankovich Deposition, dated Feb. 8, 2008.

Barth, et al., "Chapter 26.1: Measurement of Hair Growth", *Handbook of Non–Invasive Methods and the Skin*, (Serup, et al., eds.), pp. 543–547 (1995).

Bartley, et al., "An Experimental Study to Compare Methods of Eyelash Ablation", Ophthalmology, 94(10):1286–1289 (1987).

Dover, et al., "Pigmented Guinea Pig Skin Irradiated With Q–Switched Ruby Laser Pulses", Arch Dermatol., 125:43–49 (1989).

Elman, et al., "Laser Assisted Hair Removal by Selective Photothermolysis—Preliminary Results".

Finkelstein, et al., "Epilation of Hair–Bearing Urethral Grafts Using the Neodynium:YAG Surgical Laser", The Journal of Urology, 146:840–842 (1991).

Gerstman, et al., "Laser Induced Bubble Formation in the Retina", Lasers in Surgery and Medicine, 18:10–21 (1996).

Goldberg, et al., "The Use of the Frequency–doubled Q–switched Nd:YAG Laser in the Treatment of Small Cutaneous Vascular Lesions", Dermatol, 22(S41):841–844.

Goldman, et al., "Effect of the Laser Beam on the Skin. III. Exposure of Cytological Preparations", J. Invest. Dermatol., 42:247–251 (1964).

Goldman, et al., "Investigative Studies with the Laser in the Treatment of Basal Cell Epitheliomas", Southern Medical Journal, 61:735–742 (1968).

Gorisch, et al., "Laser Related Heat Effects of Blood Vessels", *Lasers in Biology and Medicine*, Hillenkamp, et al., (eds.), Plenum Press, pp. 99–109, (1980).

*Hair and Hair Diseases*, Orfanos, et al., (eds.), Springer–Verlag (1990).

Iwasaki, et al., "Development of Laser Systems for Treatment of Hyperpigmented Skin Lesions", pp. 26–34 (1989)—English Abstract.

Iwasaki, et al., "Laser–Beam Flattening Technique and Laser Systems for Treatment of Hyperpigmented Skin Lesions", UDC—English Abstract.

Japanese Article, pp. 126–130 (1990).

Klein, et al., "Session: Biological Effects of Laser Radiation I. TAM–2: Threshold Studies and Reversible Depigmentation in Rodent Skin", NEREM Record—1965, pp. 108–109 (1965).

Konig, et al., "Fluorescence Detection and Photodynamic Activity of Endogenous Protoporphyrin in Human Skin", Optical Engineering, 31(7):1470–1474 (1992).

Kuhns, et al., "Sessions: Biological Effects of Laser Radiation II", Northeast Electronics Research and Engineering Meeting—NEREM, IEEE Catalogue No. F–60, pp. 152–153 (1965).

Laor, et al., "The Pathology of Laser Irradiation of the Skin and Body Wall of the Mouse", Laser Irradiation, 47(4)643663 (1965).

Merriam–Webster Online definition of Applicator.

Mester, et al., "Effect of Laser Rays on Wound Healing", American Journal of Surgery, 122:532–535 (1971).

Mester, et al., "The Stimulating Effect of Low Power Laser–Rays on Biological Systems", Laser Review, pp. 3–6, Mar. 1968.

Moretti, et al., "Laser–Based Hair Removal", A Technology/Market Study, Medical Insight, Inc., Advertisement.

Ohshiro, The Role of the Laser in Dermatology: An Atlas, Wiley, (1997).

Optical–Thermal Response of Laser–Irradiated Tissue, Welch, et al. (eds.), Plenum Press (1995).

Oxford Encyclopedic English Dictionary, p. 15 (1995).

Palomar Medical Technologies, Inc., "Medical and Technical Aspects of Laser Hair Removal", printed from http://www.thegentletouch.com/laser.med–asp.htm, printed Sep. 16, 1998.

Randall, et al., "Seasonal Changes in Human Hair Growth", British Journal of Dermatology, 124:146–151 (1991).

Saitoh, et al., "Human Hair Cycle", Journal of Investigative Dermatology, 54(1):65–81 (1970).

Stedman's Concise Medical Dictionary for the Health Professions, 4th Edition, pp. 140, 365, 890, 986 (2001).

Stedman's Medical Dictionary, 23rd Edition, pp. 203, 204 (1979).

Stedman's Medical Dictionary, 26th Edition, pp. 251–252 (1995).

Vines, "Get Under Your Skin",Inside Science, Jan., pp. 1–4 (1995).

Welch, et al., "Chapter Eighteen: Introduction to Medical Applications", *Optical–Thermal Response of Laser–Irradiated Tissue*, Welch, et al., (eds.), Plenum Press, pp. 609–618 (1995).

Welch, et al., "Chapter One: Overview of Optical and Thermal Laser–Tissue Interaction and Nomenclature", *Optical–Thermal Response of Laser–Irradiated Tissue*, Welch, et al., (eds), Plenum Press, pp. 1–12 (1995).

Welch, et al., "Chapter Twenty–Six: Summary and Future", *Optical–Thermal Response of Laser–Irradiated Tissue*, Welch, et al. (eds.), Plenum Press, pp. 903–912 (1994).

Zeitler, et al., "Chapter 1: Laser Characteristics that Might Be Useful in Biology", Laser Applications in Medicine and Biology, vol. I, (Wolbarsht, ed.), Plenum Press, pp. 1–18 (1971).

Saitoh, et al. "Human Hair Cycle", Journal of Investigative Dermatology, 54(1):65–81 (1970).

Margolis, et al., "Visible Action Spectrum for Melanin–Specific Selective Photothermolysis", Lasers in Surgery and Medicine, 9:389–397 (1989).

Philipp, et al., "Treatment of Congenital Vascular Disorders—Classification, Step Programme and Therapeutic Procedures", SPIE, 2086:228–238 (1993).

Goldman, "Surgery by Laser for Malignant Melanoma", J. Dermatol. Surg. Oncol., 5(2):141–144 (1979).

Goldman, *Biomedical Aspects of the Laser*, Springer–Verlag, ppl. iii–11 and 220–232 (1967).

Goldman, et al., "Laser Action at the Cellular Level", JAMA, 198:641–644 (1966).

Goldman, et al., "Laser Treatment of Tattoos", JAMA, 201(11):163–166 (1967).

Goldman, et al., "Long–Term Laser Exposure of a Senile Freckle", Arch Environ Health, 22:401–403 (1971).

Goldman, et al., "Treatment of Basal Cell Epithelioma by Laser Radiation", JAMA, 189:773–775 (1964).

Margolis, et al., "Visible Action Spectrum for Melanin–Specific Selective Photothermolysis", Lasers in Surgery and Medicine, 9:389–397 (1989).

Philipp, et al., "Treatment of Congenital Vascular Disorders—Classification, Step Programme and Therapeutic Procedures", SPIE, 2086:228–238 (1993).

Seago, et al., "The Hair Cycle on the Human Thigh and Upper Arm", British Journal of Dermatology, 113:9–16 (1985).

Brief of Asclepion of Apr. 6, 2009, filed in Opposition EP 02076294.4–2305/1230900, with English Translation (7 pages).

Brief of Carl Zeiss Meditec of Apr. 9, 2009, filed in Opposition EP 96906222.3–2305/0806913, with English translation (5 pages).

Communication under Rule 51(4) EPC, Application No. 96 906 222.3–2305, dated Feb. 22, 2002 (40 pages).

Decision Revoking the European Patent EP–B–0806913 (23 pages).

Interlocutory Decision in Opposition Proceedings, Opposition 96 906 222.3–2305/806913 (37 pages).

Minutes of the Oral Proceedings before the Opposition Division, Opposition 96 906 222.3 (7 pages).

Minutes of the Oral Proceedings before the Opposition Division, Opposition EP 02 076 294.4 (8 pages).

"Summons to Attend Oral Proceedings Pursuant to Rule 71(1) EPC" issued in Opposition EP 96906222.3–1204/0806913, dated Apr. 27, 2004 (8 pages).

Interlocutory Decision in Opposition Proceedings, Opposition 02 076 294.4–2305/1230900 (39 pages).

Response to Asclepion Brief dated Apr. 6, 2009, in EP 1 230 900; Response filed Apr. 29, 2009 (4 pages).

Response to Carl Zeiss Meditec brief, dated Apr. 9, 2009, in EP 0 806 913; Response dated Apr. 29, 2009 (3 pages).

Response to Examiner's Report dated Mar. 5, 2001 in EP 96906222.3–2305; Response filed Nov. 9, 2001 (8 pages).

Response to Oppositions filed against EP 0 806 913 on Apr. 22, 2003; Response filed Dec. 19, 2003 (4 pages).

Response to Oppositions filed against EP 0 565 331; Response dated Nov. 24, 2004 (2 pages).

Leon Goldman, M.D., "Biomedical Aspects of the Laser", Springer–Verlag, New York, Inc. (1967), pp. 24.

John Harvey Kellogg, M.D., "Light Therapeutic: A Practical Manual of Phototherapy for the Student and the Practitioner," The Modern Medicine Pub. Co., Battle Creek, MI (1927), pp. 11.

Leon Goldman, M.D. and R. James Rockwell, Jr., "Lasers in Medicine," Gordon and Breach, Science Publishers, Inc. (1971), pp. 4.

R. Rox Anderson, B.S. and John A. Parrish, M.D., "The Optics of Human Skin," The Journal of Investigative Dermatology, vol. 77, No. 1, Jul. 1981, pp. 13–19.

"Selective Photothermolysis: Precise Microsurgery by Selective Absorption of Pulsed Radiation," Science, vol. 220, Apr. 29, 1983, pp. 524–527.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–10, 13, 14 and 18–21 is confirmed.

New claims 23 and 24 are added and determined to be patentable.

Claims 11, 12, 15–17 and 22 were not reexamined.

23. The method of claim 1, wherein the optical radiation has a pulse duration of between 50 μs and 200 ms.

24. The method of claim 1, wherein the transparent device is sapphire.

* * * * *